United States Patent
Chung et al.

(10) Patent No.: US 9,969,978 B2
(45) Date of Patent: May 15, 2018

(54) METHOD FOR PRODUCING CARDIOMYOCYTES FROM HUMAN OR MOUSE EMBRYONIC STEM CELLS IN A MEDIUM CONSISTING OF A SERUM-FREE MEDIUM AND N2 SUPPLEMENT

(71) Applicant: CHABIO & DIOSTECH CO., LTD., Gyeonggi-do (KR)

(72) Inventors: Hyung Min Chung, Seoul (KR); Sung Hwan Moon, Seoul (KR)

(73) Assignee: Chabio & Diostech Co., Ltd, Gyeonggi-do (KR)

( * ) Notice: Subject to any disclaimer, the term of this patent is extended or adjusted under 35 U.S.C. 154(b) by 0 days. days.

(21) Appl. No.: 13/907,967

(22) Filed: Jun. 2, 2013

(65) Prior Publication Data
US 2013/0251691 A1 Sep. 26, 2013

Related U.S. Application Data

(63) Continuation of application No. PCT/KR2011/007408, filed on Oct. 6, 2011.

(30) Foreign Application Priority Data

Oct. 6, 2010 (KR) .................. 10-2010-0097543

(51) Int. Cl.
*C12N 5/071* (2010.01)
*C12N 5/077* (2010.01)
*A61K 35/34* (2015.01)

(52) U.S. Cl.
CPC ............ *C12N 5/0657* (2013.01); *A61K 35/34* (2013.01); *C12N 2506/02* (2013.01)

(58) Field of Classification Search
CPC ............... C12N 5/0606; C12N 5/0657; C12N 2500/99; C12N 2506/02; A61K 35/34
See application file for complete search history.

(56) References Cited

U.S. PATENT DOCUMENTS

2003/0031651 A1  2/2003  Lee et al.

FOREIGN PATENT DOCUMENTS

GB           2427873 B       1/2007
WO    WO 2005090558 A1  *  9/2005

OTHER PUBLICATIONS

Doevendans et al. "Differentiation of Cardiomyocytes in Floating Embryoid Bodies is Comparable to Fetal Cardiomyocytes." J Mol Cell Cardiol. (2000), 32 (5); pp. 839-851.*
Lu et al. "Avian-induced pluripotent stem cells derived using human reprogramming factors . . . " Stem Cells Dev. (Feb. 2012);21(3): pp. 394-403. Epub Nov. 16, 2011.*
Xu et al. "Feeder-free growth of undifferentiated human embryonic stem cells." Nature Biotechnology (2001);19: pp. 971-974.*
Xu et al. "Basic Fibroblast Growth Factor Supports Undifferentiated Human Embryonic Stem Cell Growth Without Conditioned Medium." Stem Cells. (Mar. 2005); 23(3):pp. 315-323.*
Vackova et al. "Putative embryonic stem cell lines from pig embryos." J Reprod Dev. (Dec. 2007);53(6): pp. 1137-1149.*
Huber, I., et al., "Identification and selection of cardiomyocytes during human embryonic stem cell differentiation," The FASEB Journal, vol. 21, No. 10, pp. 2551-2563 (Aug. 2007).
Ulloa-Montoya, F., et al., "Culture Systems for Pluripotent Stem Cells," Journal of Bioscience and Bioengineering, vol. 100, No. 1, pp. 12-27, The Society for Biotechnology, Japan (2005).
Yao, S., et al., "Long-term self-renewal and directed differentiation of human embryonic stem cells in chemically defined conditions" PNAS, vol. 103, No. 18, pp. 6907-6912 (May 2, 2006).
International Search Report with Written Opinion for International Application No. PCT/KR2011/007408 dated Apr. 19, 2012.

* cited by examiner

*Primary Examiner* — Titilayo Moloye
(74) *Attorney, Agent, or Firm* — Henry J. Cittone; Cittone Demers & Arneri

(57) ABSTRACT

The present invention relates to a method for producing embryonic stem cell-derived cardiomyocytes, cardiomyocytes produced by the method, a method for producing cardiomyocyte bodies from the cardiomyocytes, cardiomyocyte bodies produced by the method, a cellular therapeutic agent comprising the cardiomyocyte bodies as an active ingredient for the treatment of cardiac diseases, a method for treating cardiac diseases using the cellular therapeutic agent, and use of cardiomyocytes or cardiomyocyte bodies for the preparation of the cellular therapeutic agent. The method for producing cardiomyocytes of the present invention can be used to easily purify differentiated cardiomyocytes from embryonic stem cells. Further, the purified cardiomyocytes can be used to produce cardiomyocyte bodies, which can be used as a cellular therapeutic agent for treating cardiac diseases. Therefore, the cardiomyocyte bodies can be widely applied to the development of prophylactic or therapeutic agents for cardiac diseases.

8 Claims, 39 Drawing Sheets

[FIG. 1]
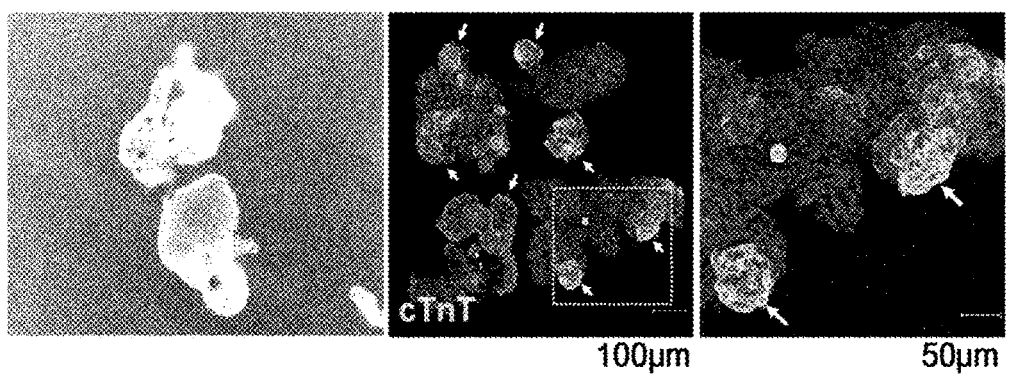
[FIG. 2]
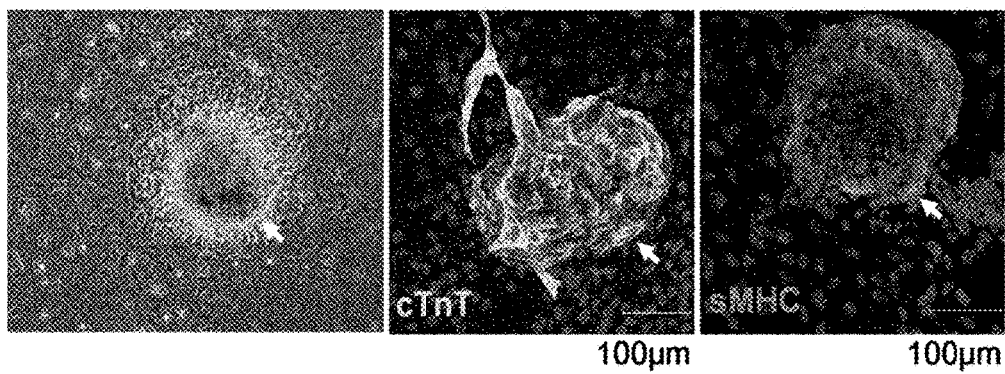

[FIG. 3a]
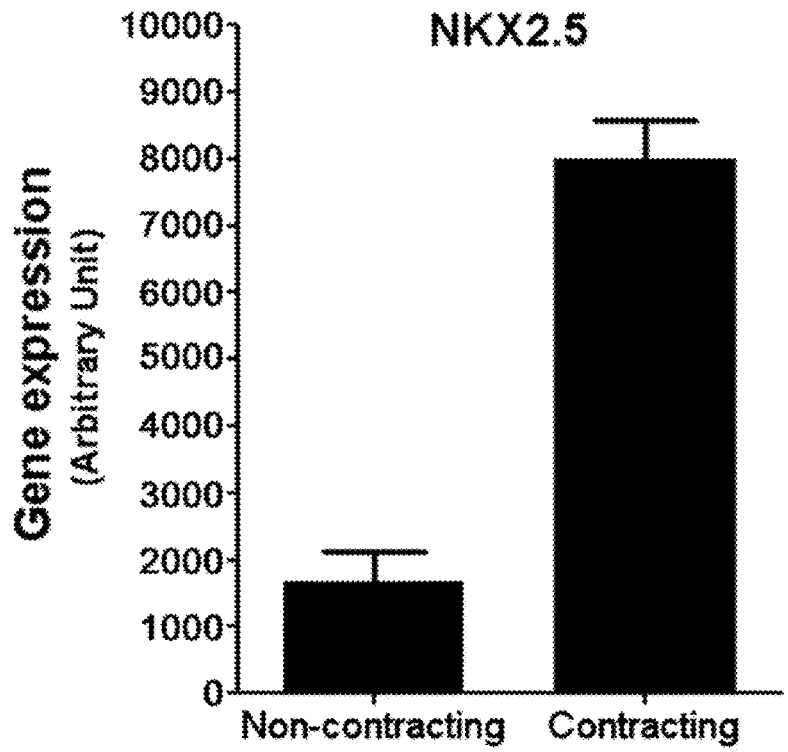
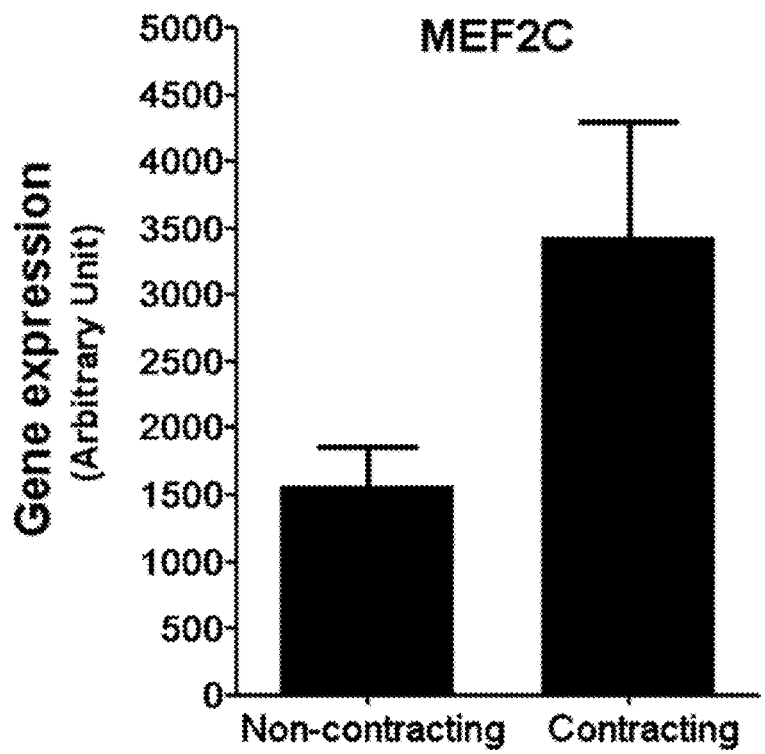

[FIG. 3b]
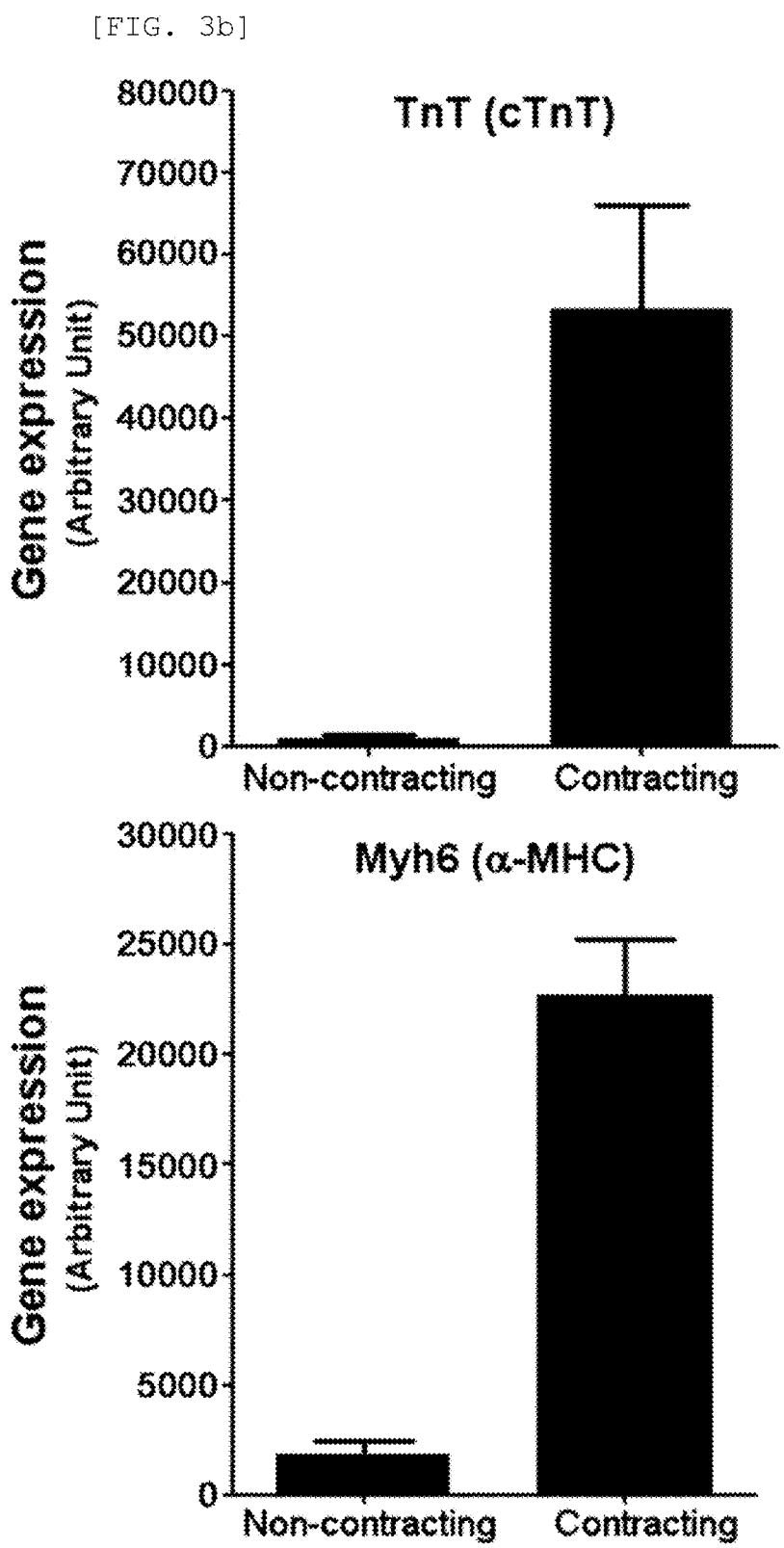

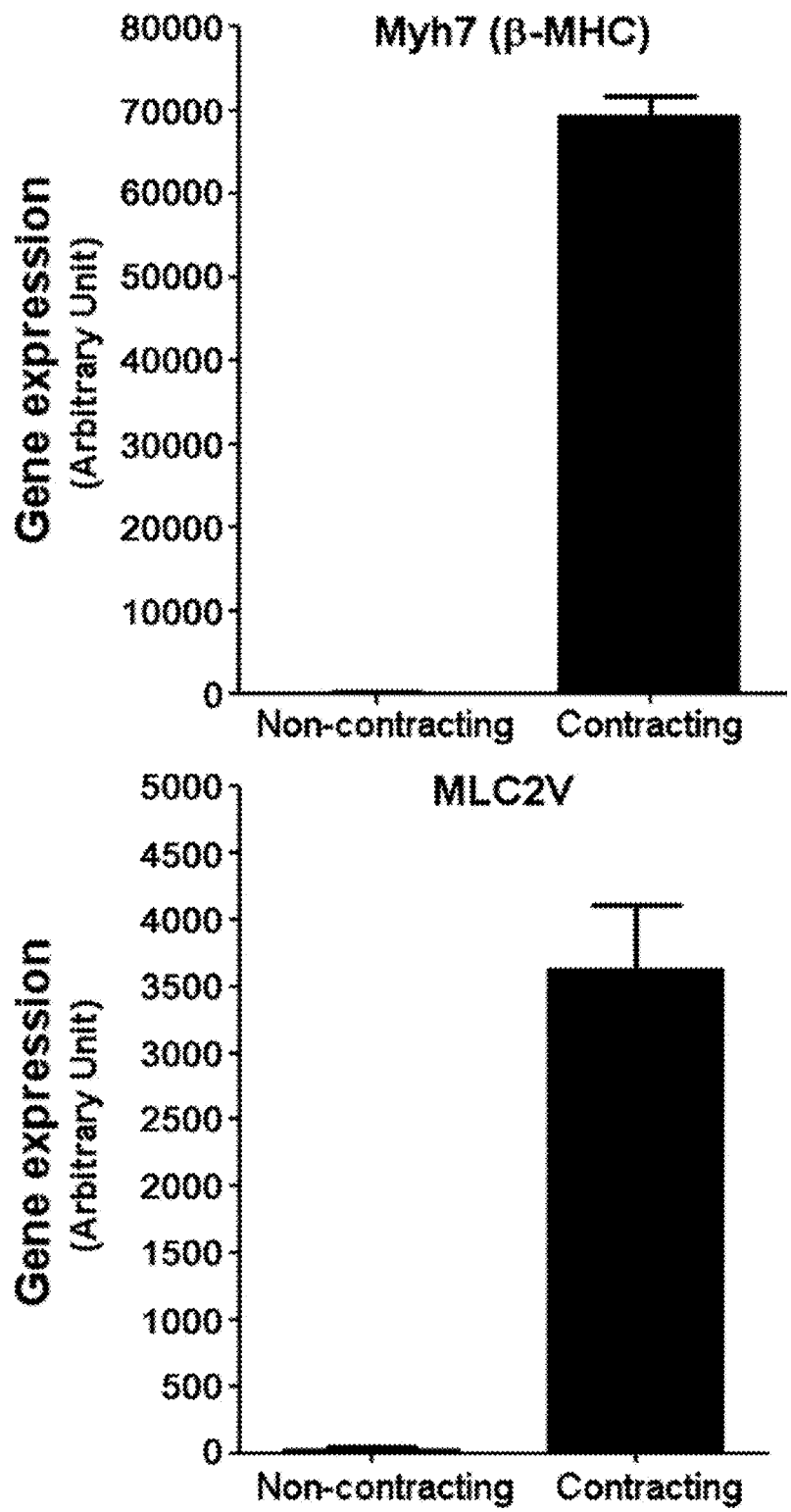
[FIG. 3c]

[FIG. 4]
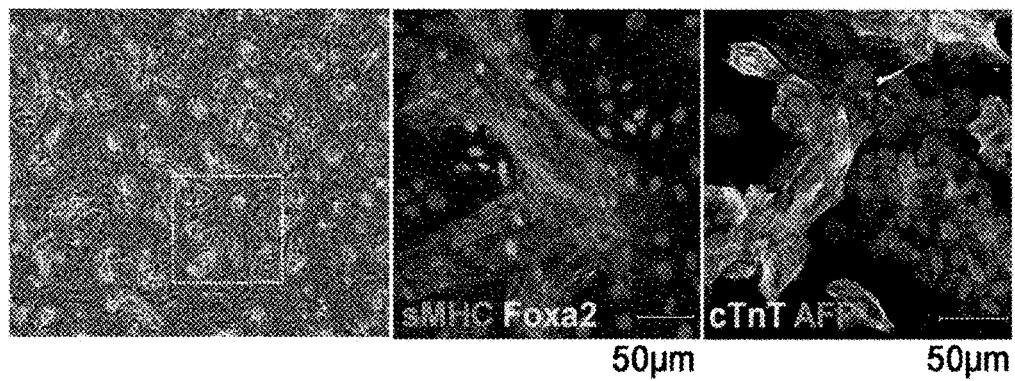
[FIG. 5]
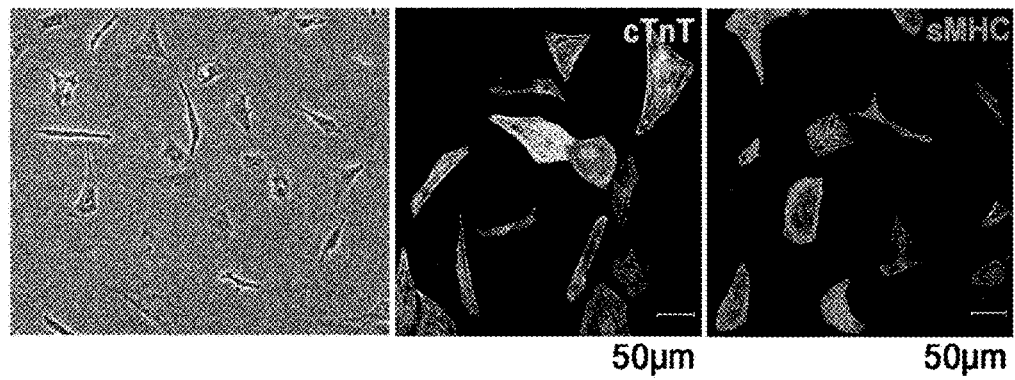

[FIG. 6]
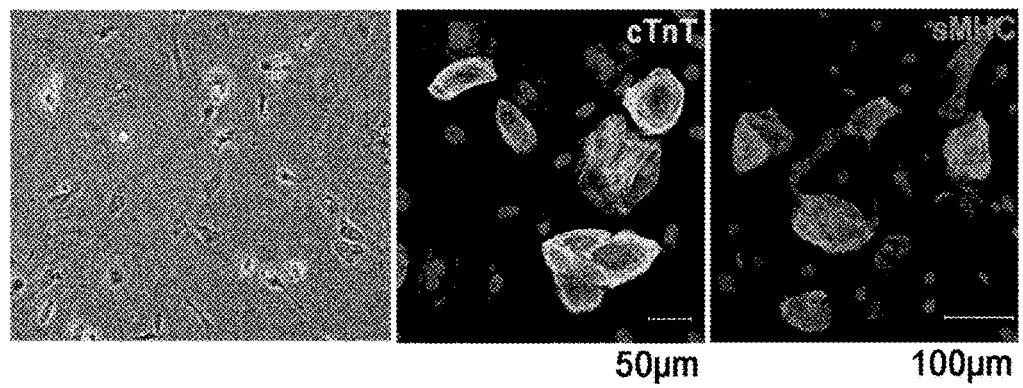
[FIG. 7]
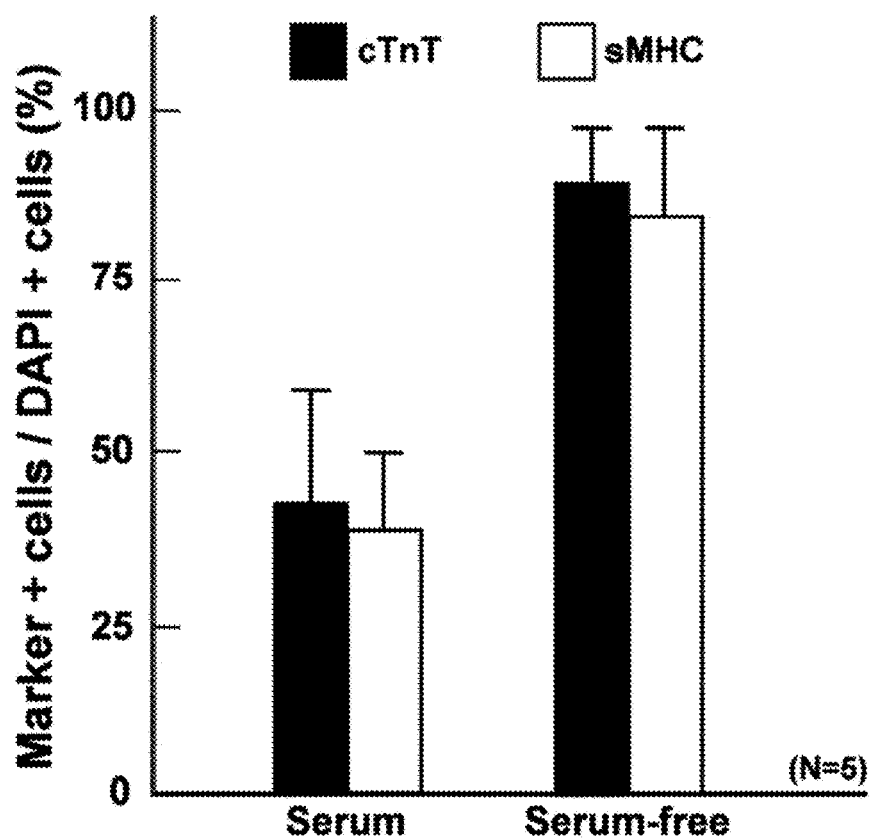

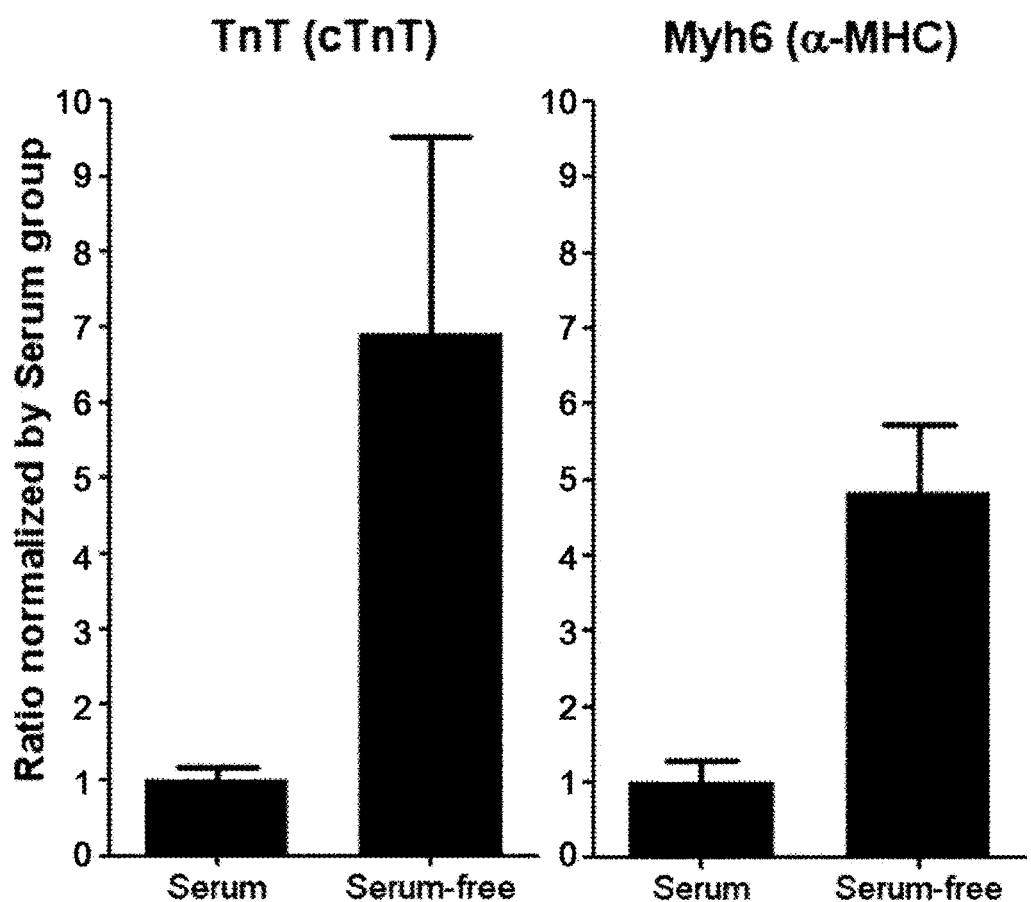

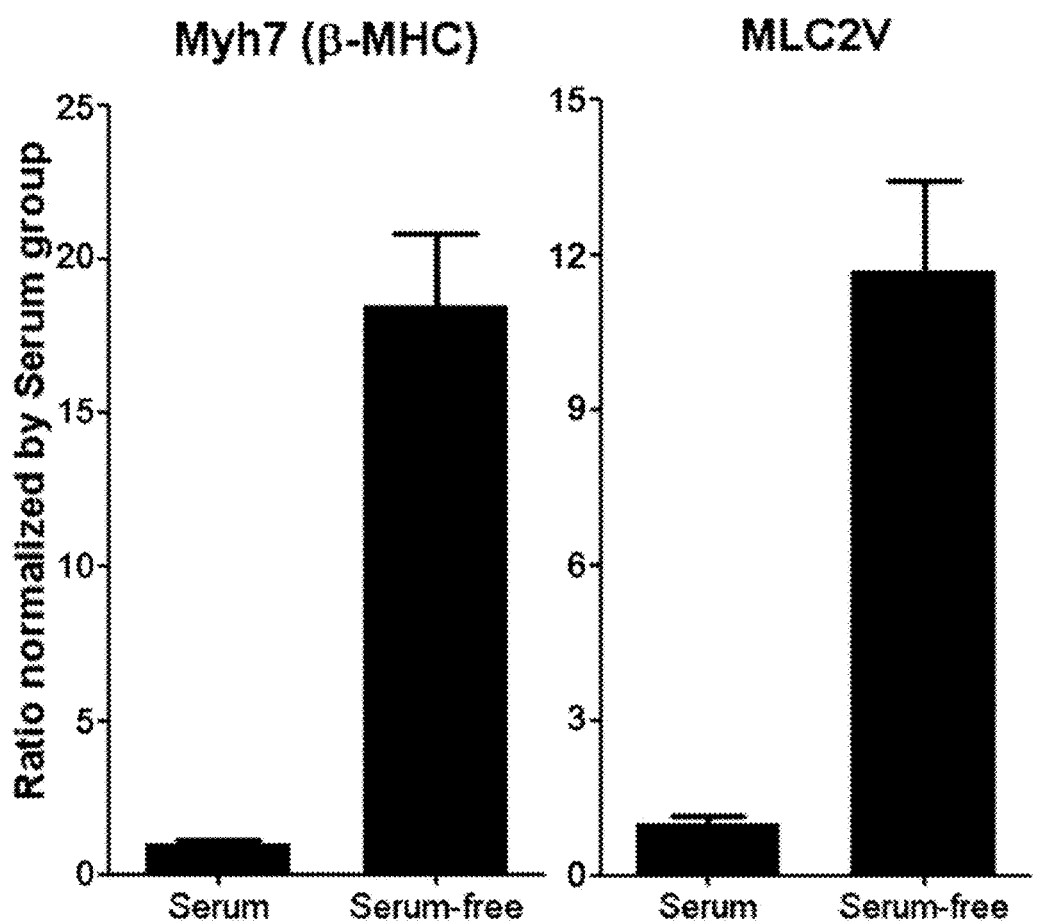
[FIG. 8b]

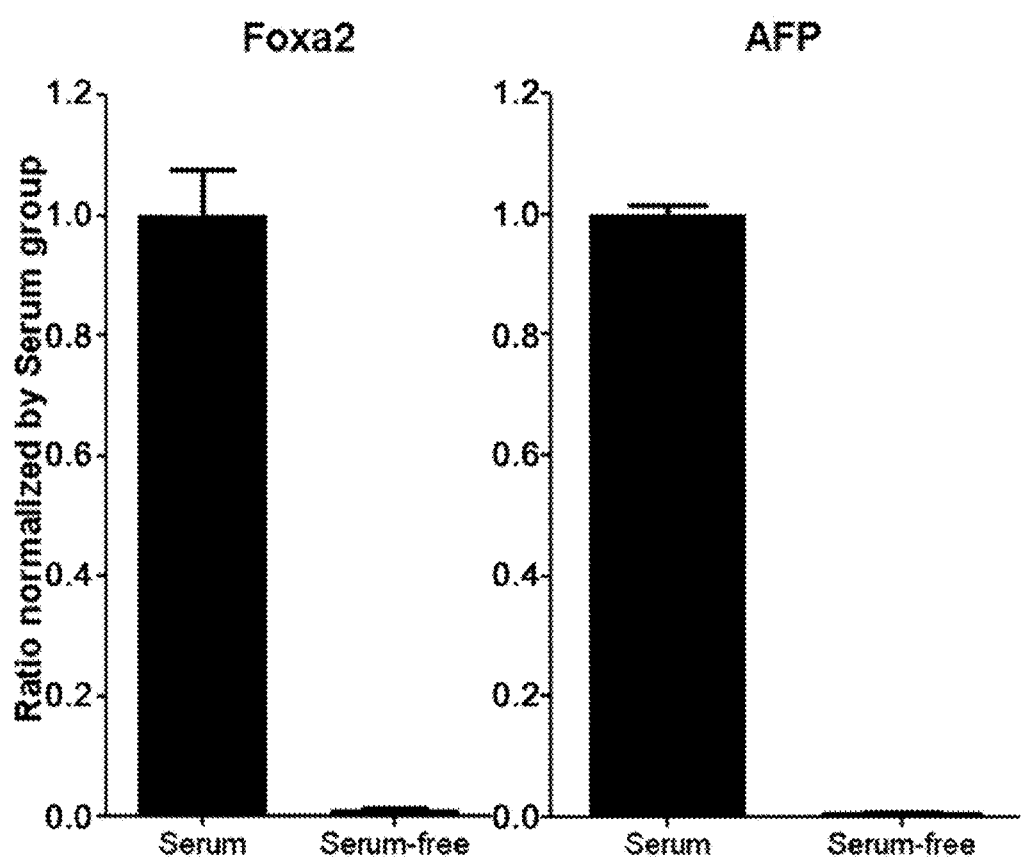
[FIG. 8c]

[FIG. 9]
Ventricular-type
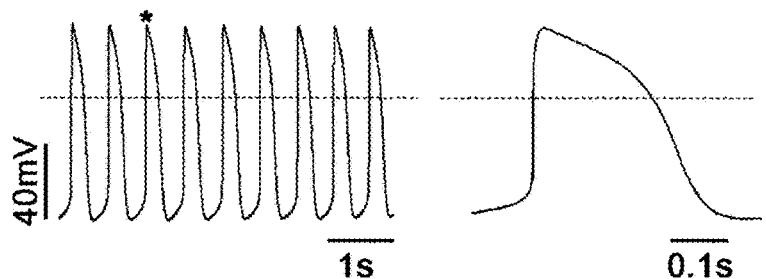
Atrial-type
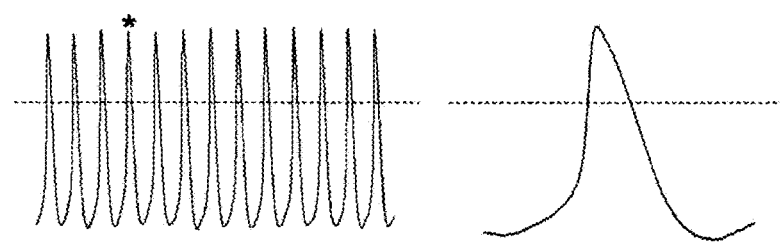
Nodal-type
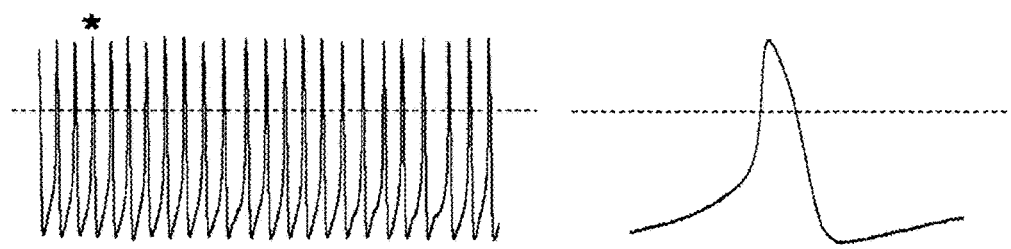

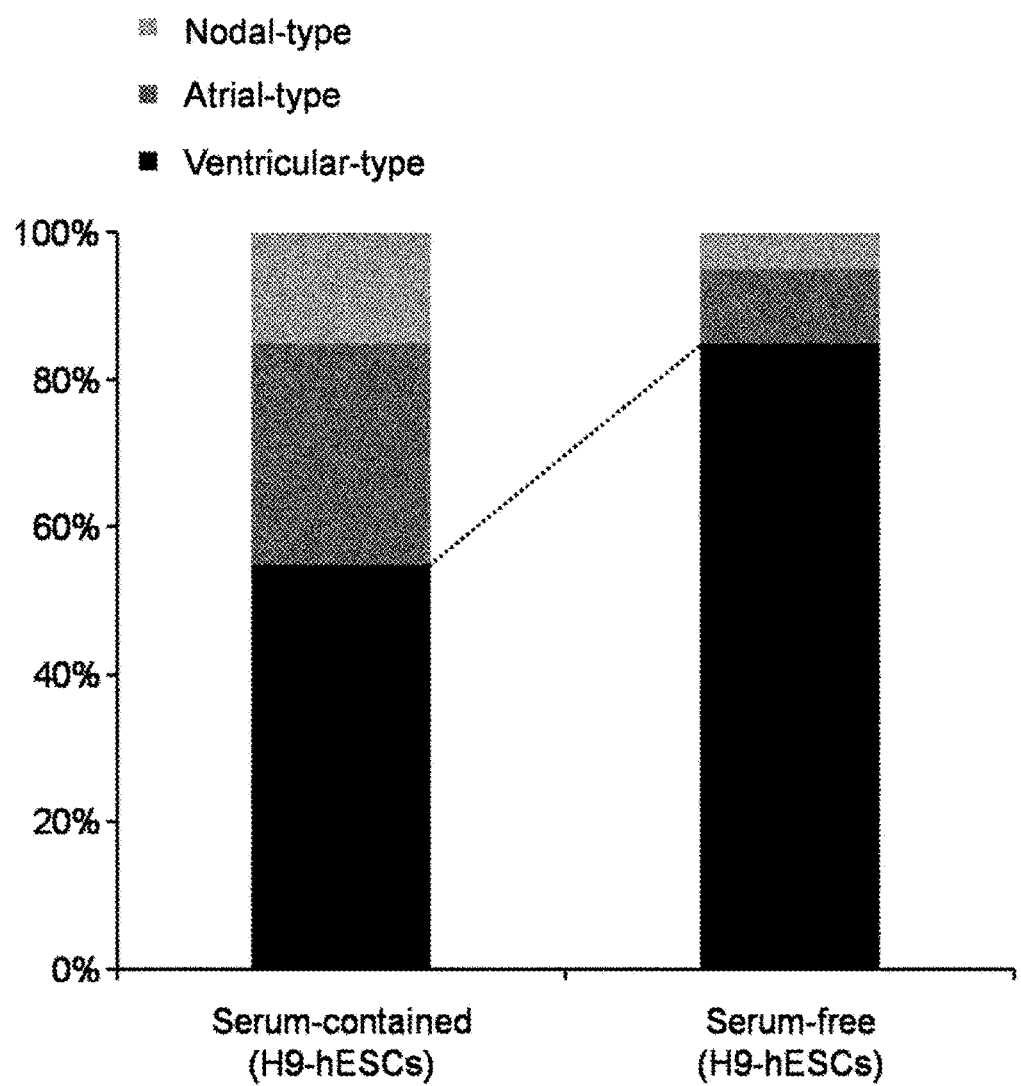

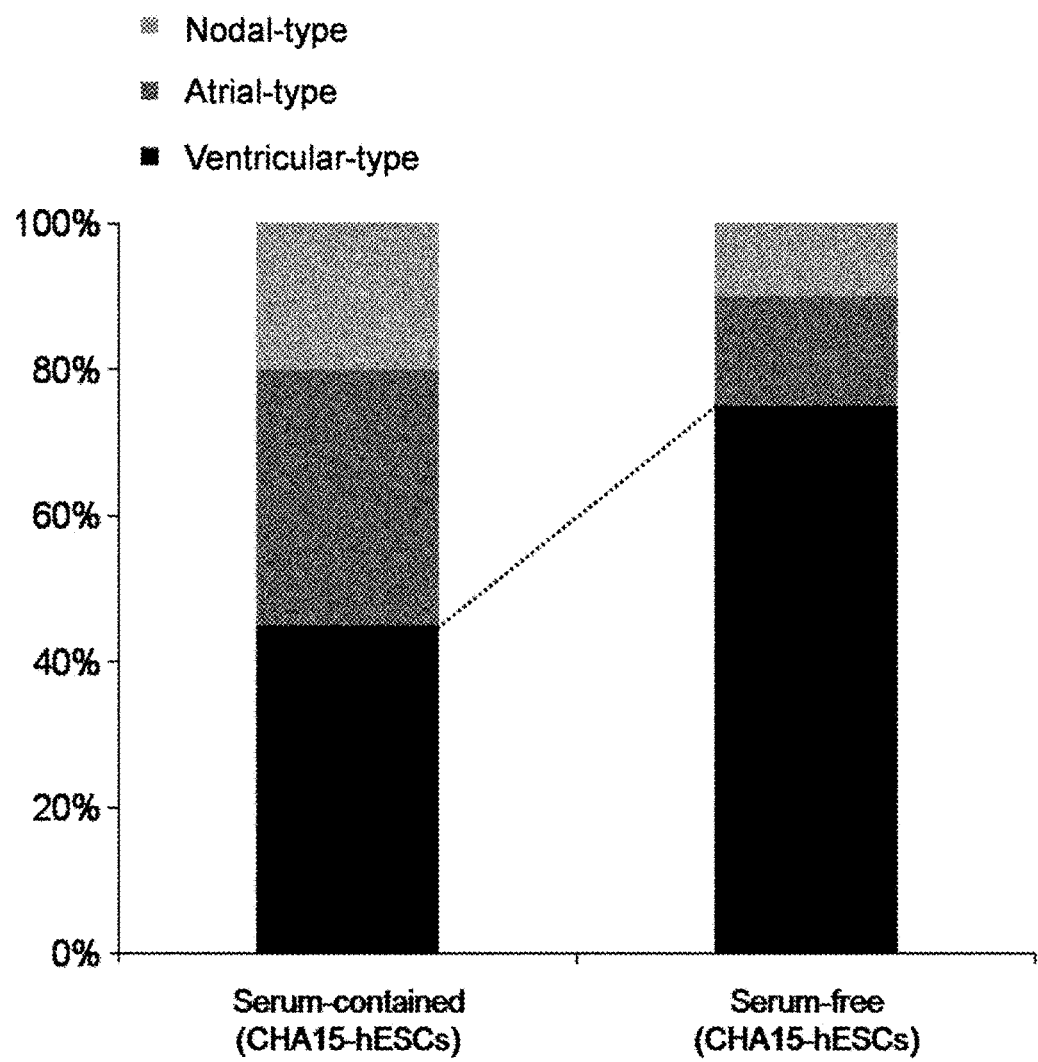
[FIG. 11]

[FIG. 12]
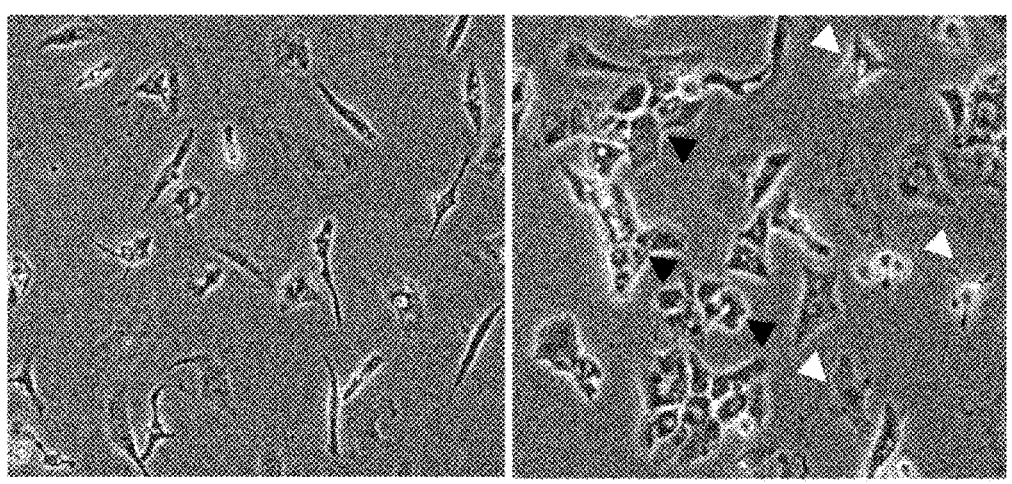

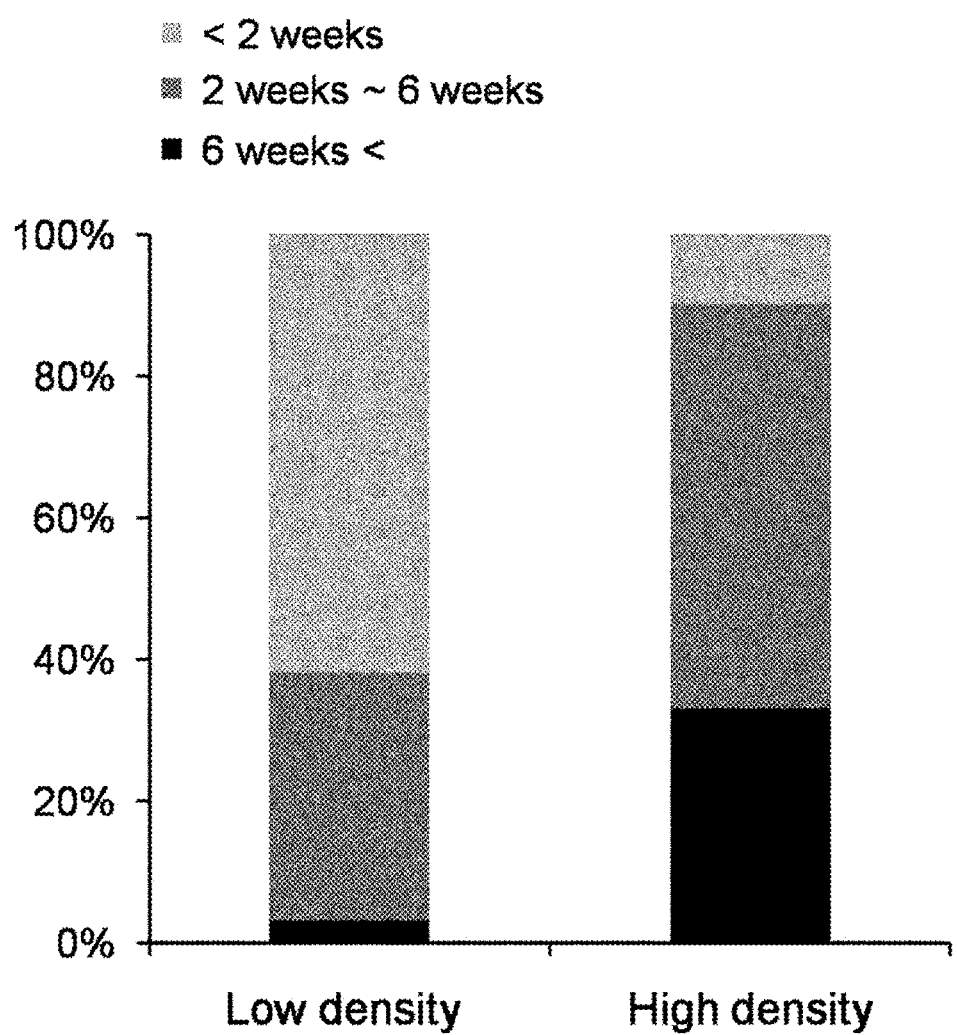
[FIG. 13]

[FIG. 14]
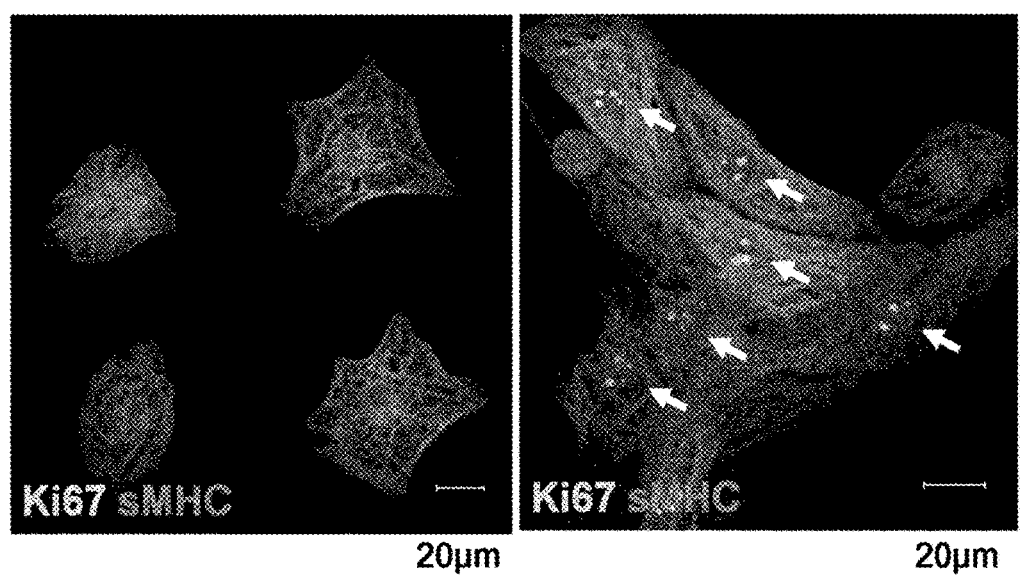

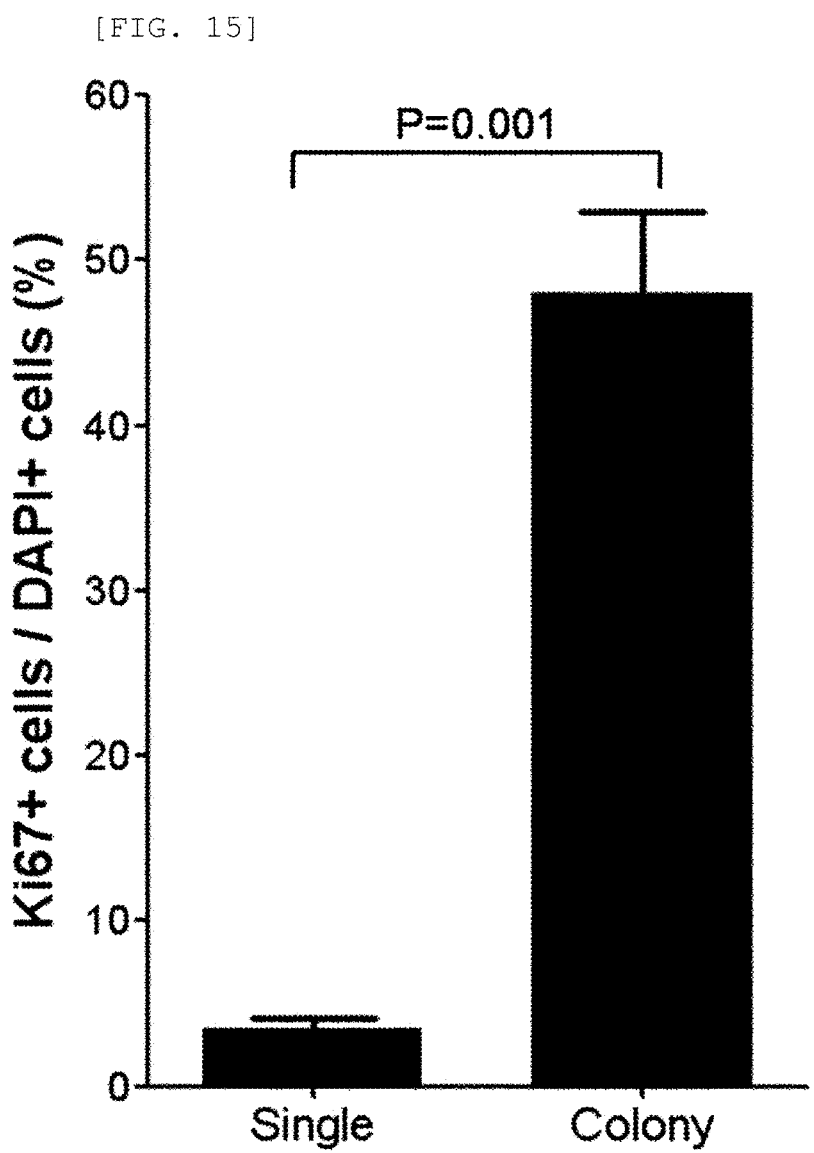
[FIG. 15]

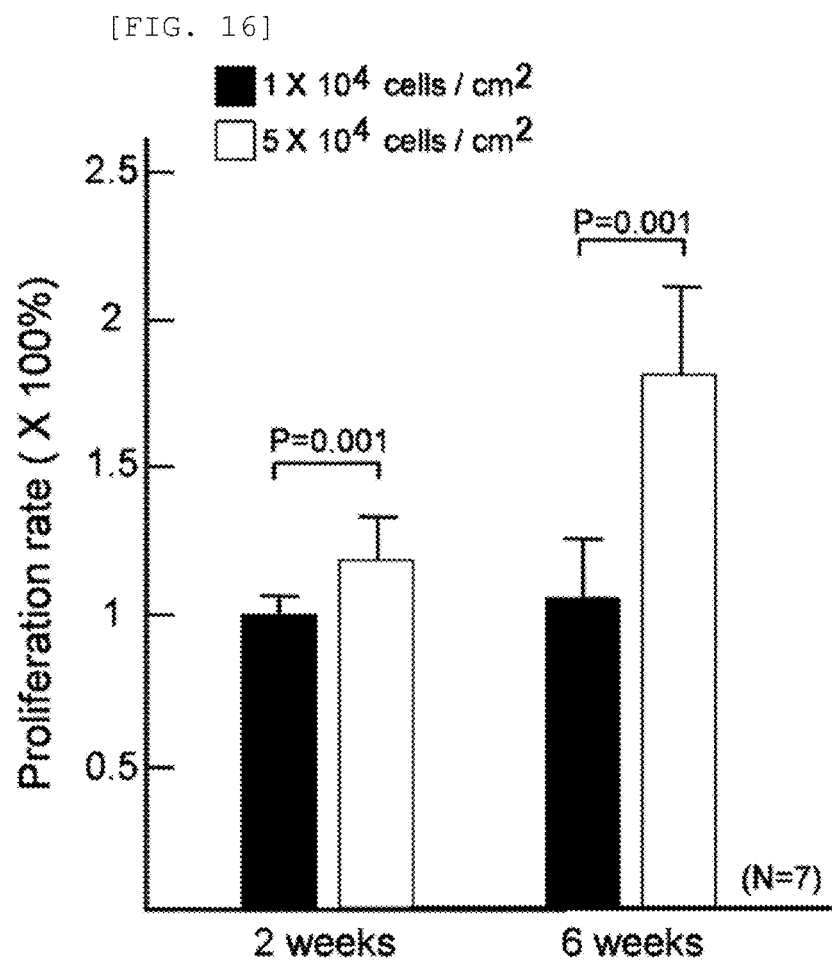
[FIG. 16]

[FIG. 17]
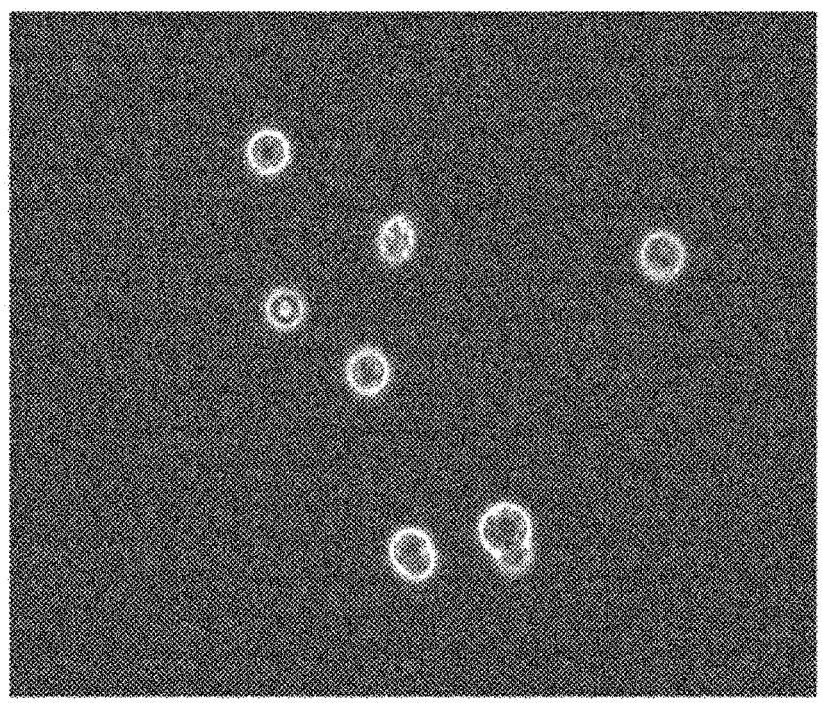

[FIG. 18]
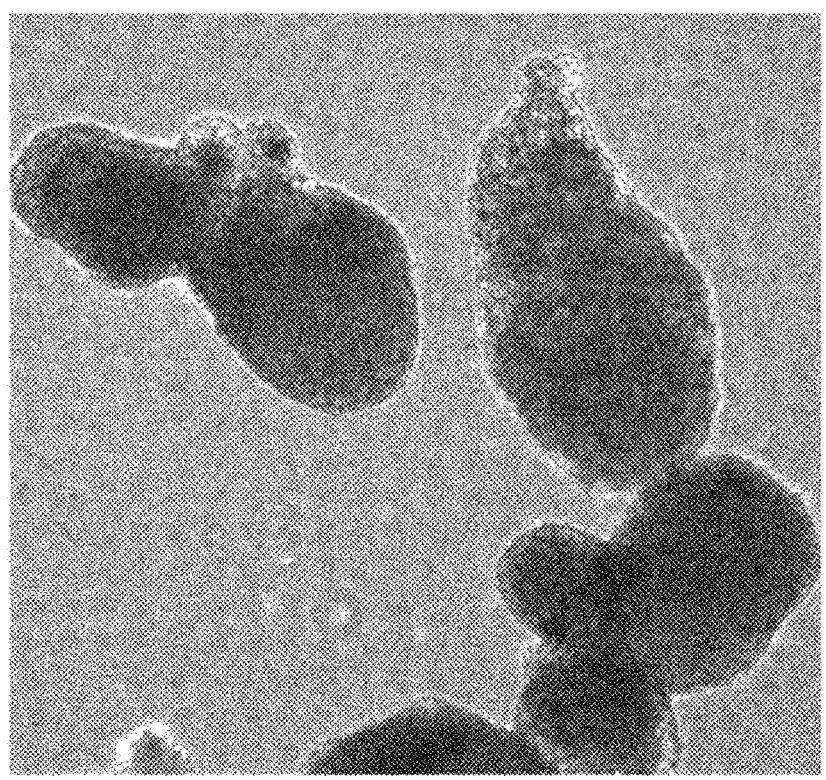

[FIG. 19]
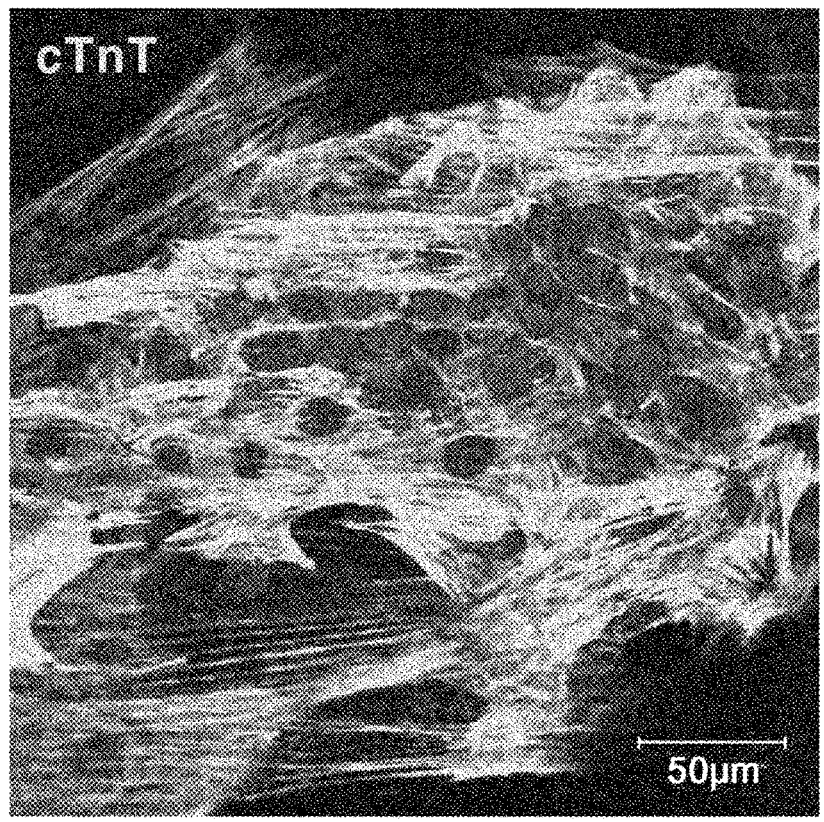

[FIG. 20]
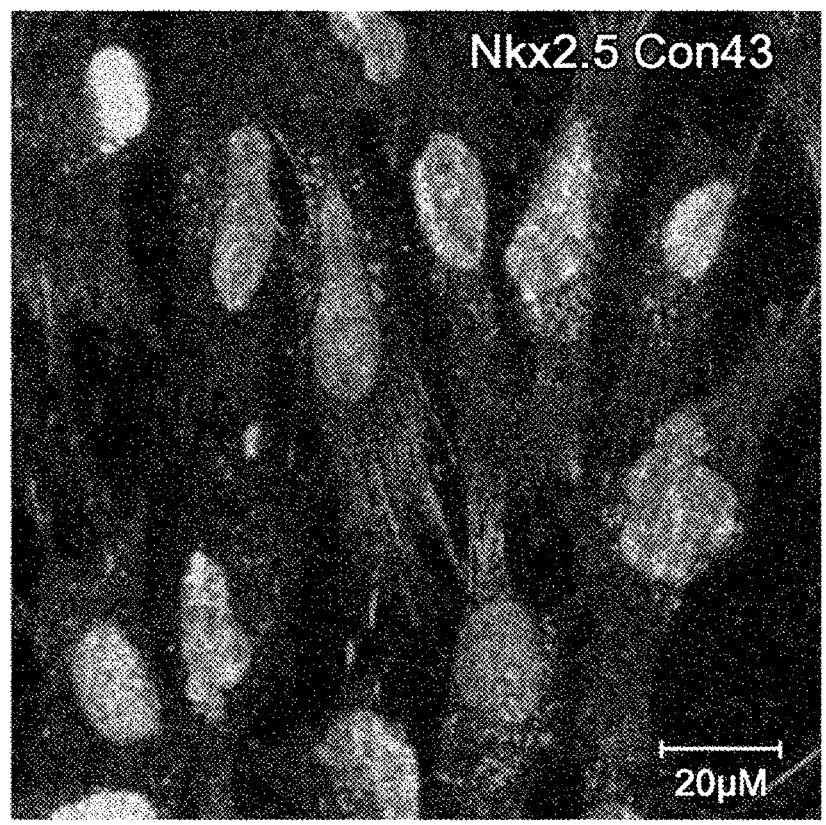

[FIG. 21]
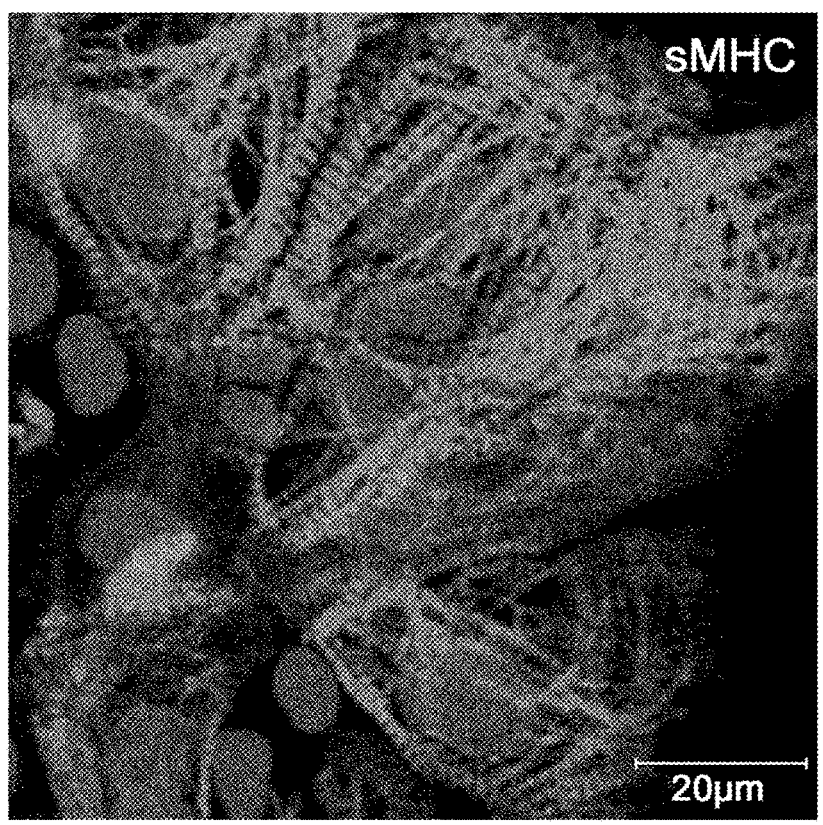

[FIG. 22]
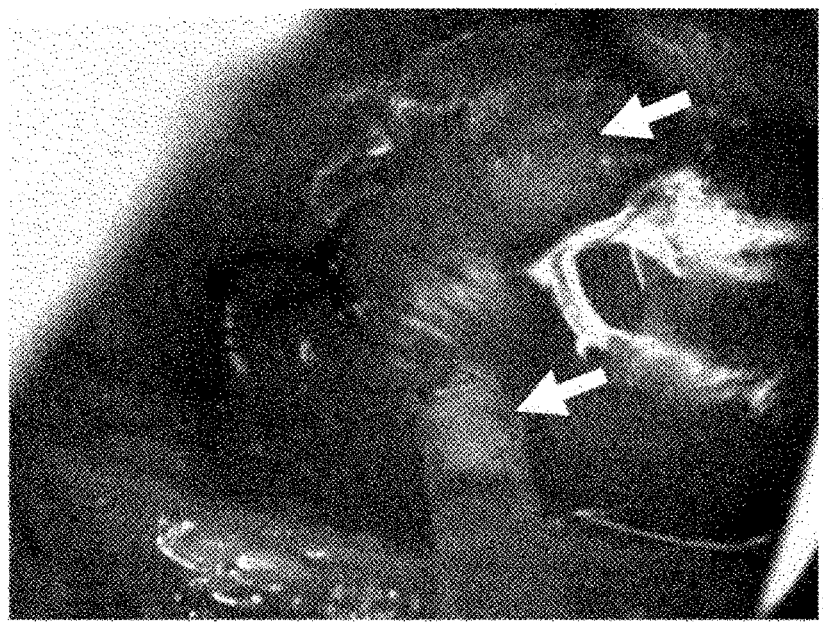

[FIG. 23]
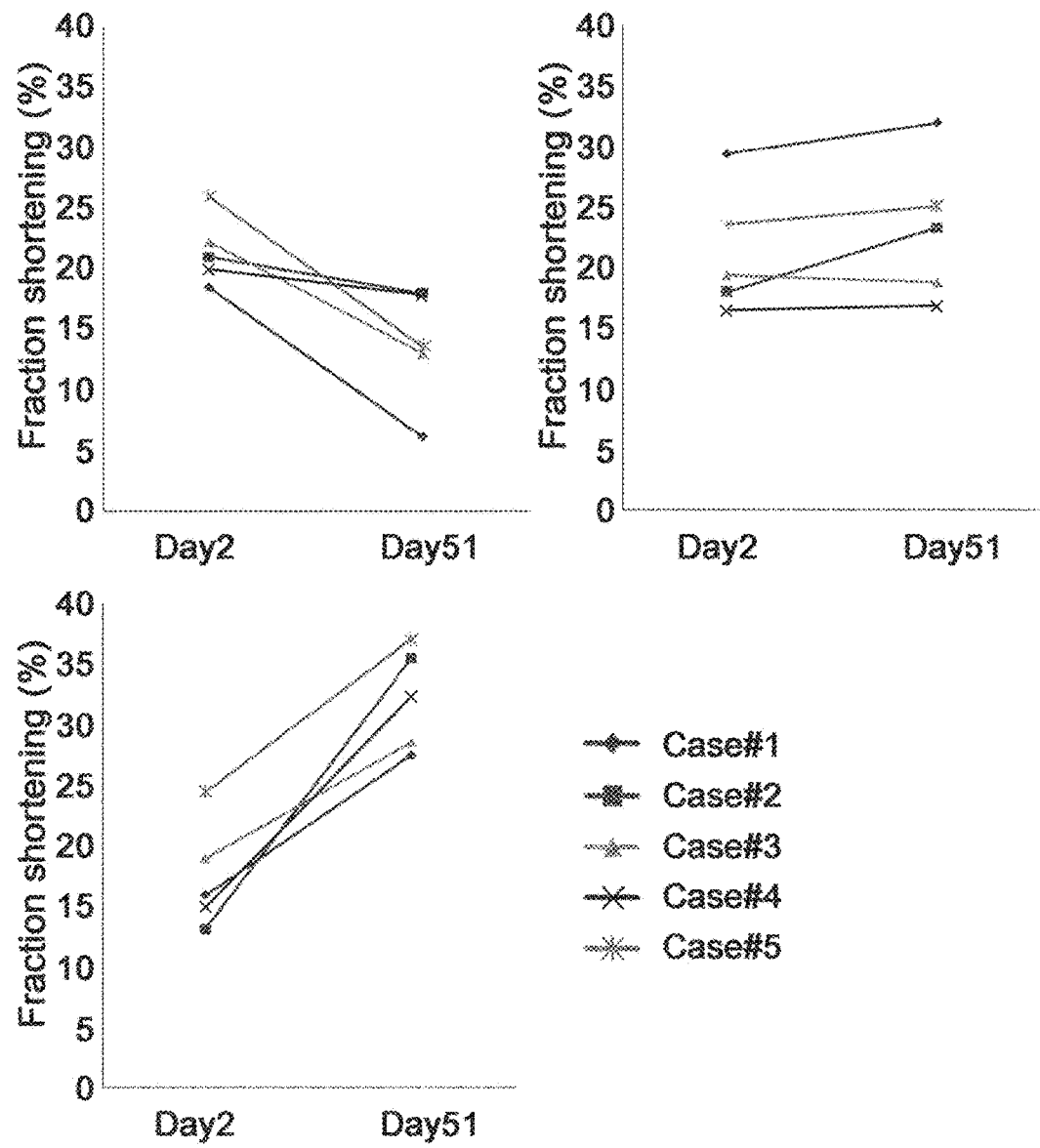

[FIG. 24]
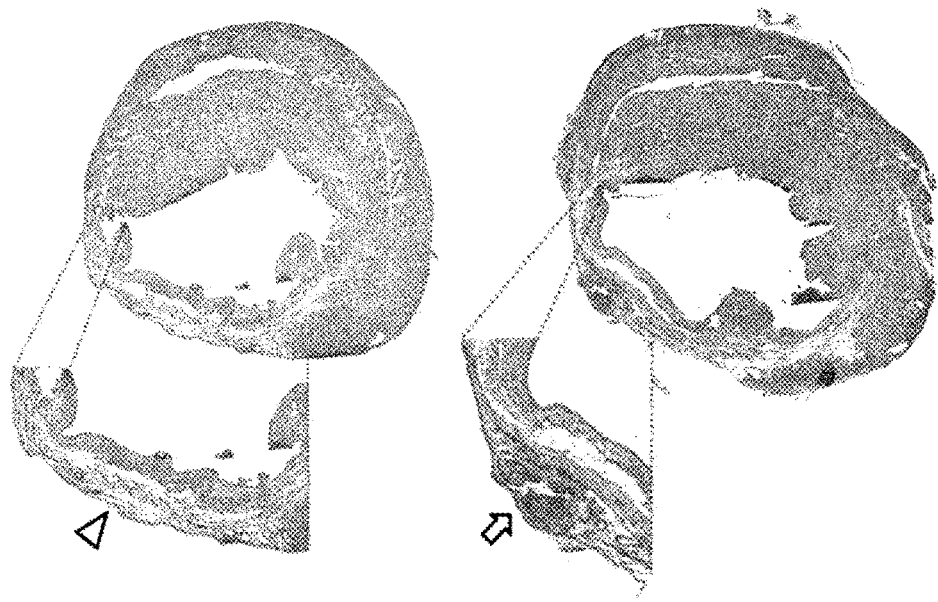
[FIG. 25]
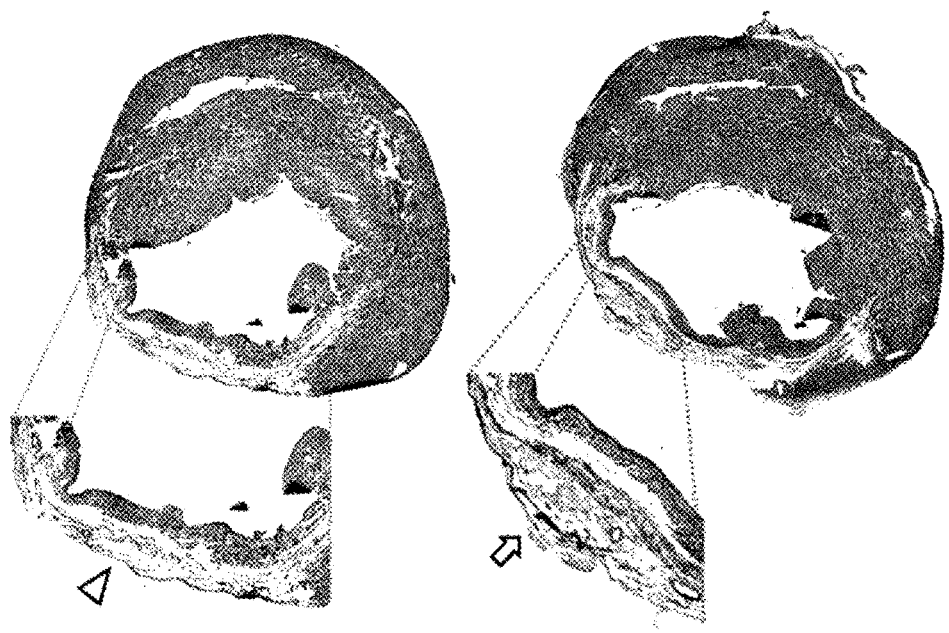

[FIG. 26]
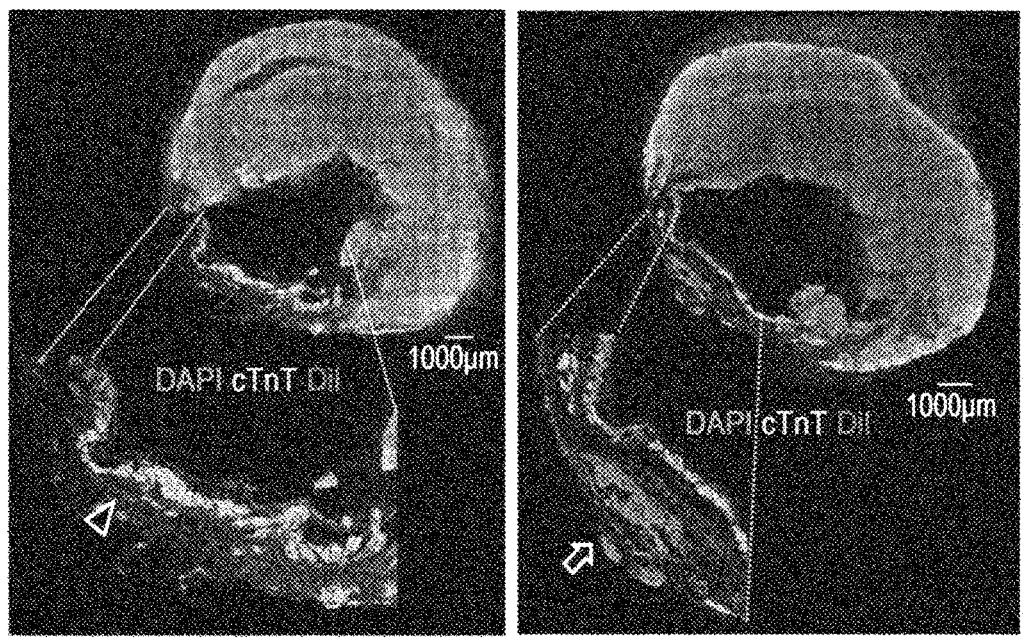

[FIG. 27]
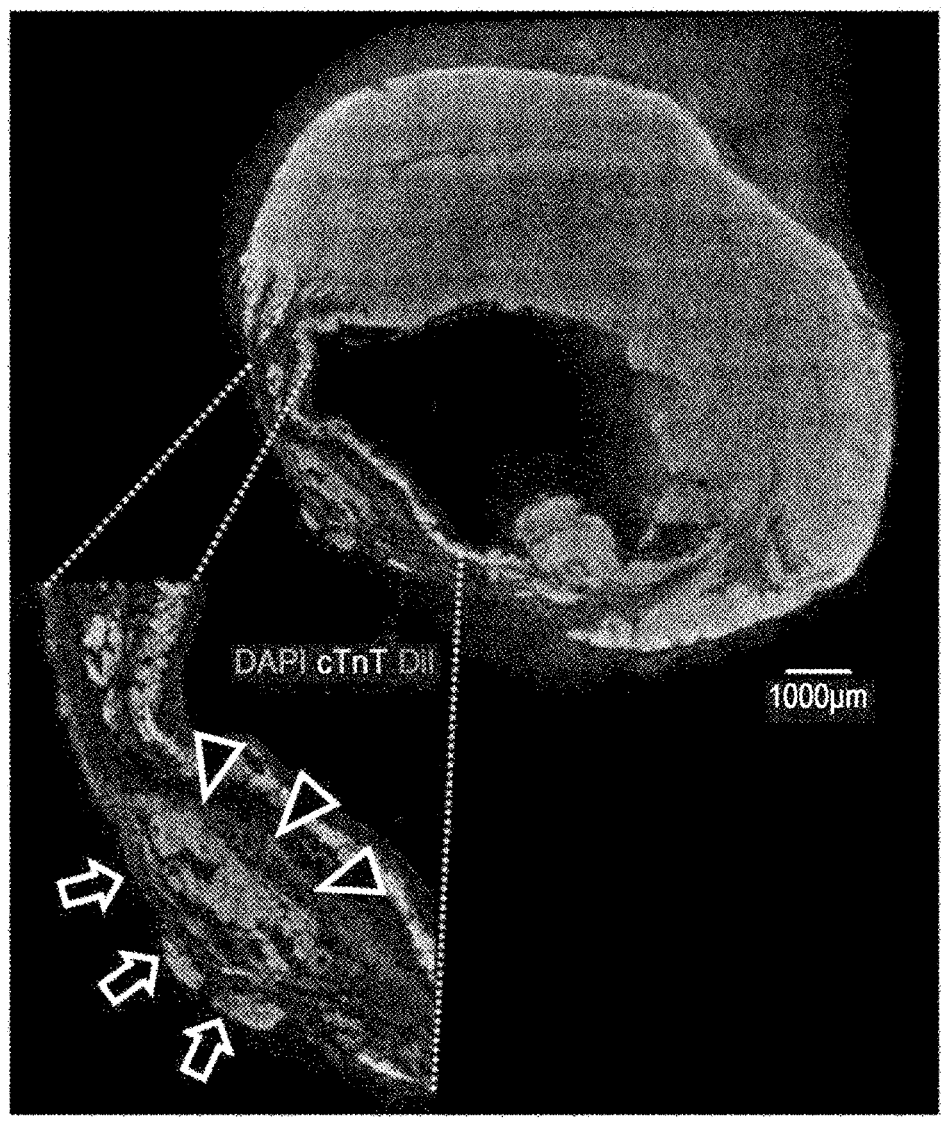

[FIG. 28]
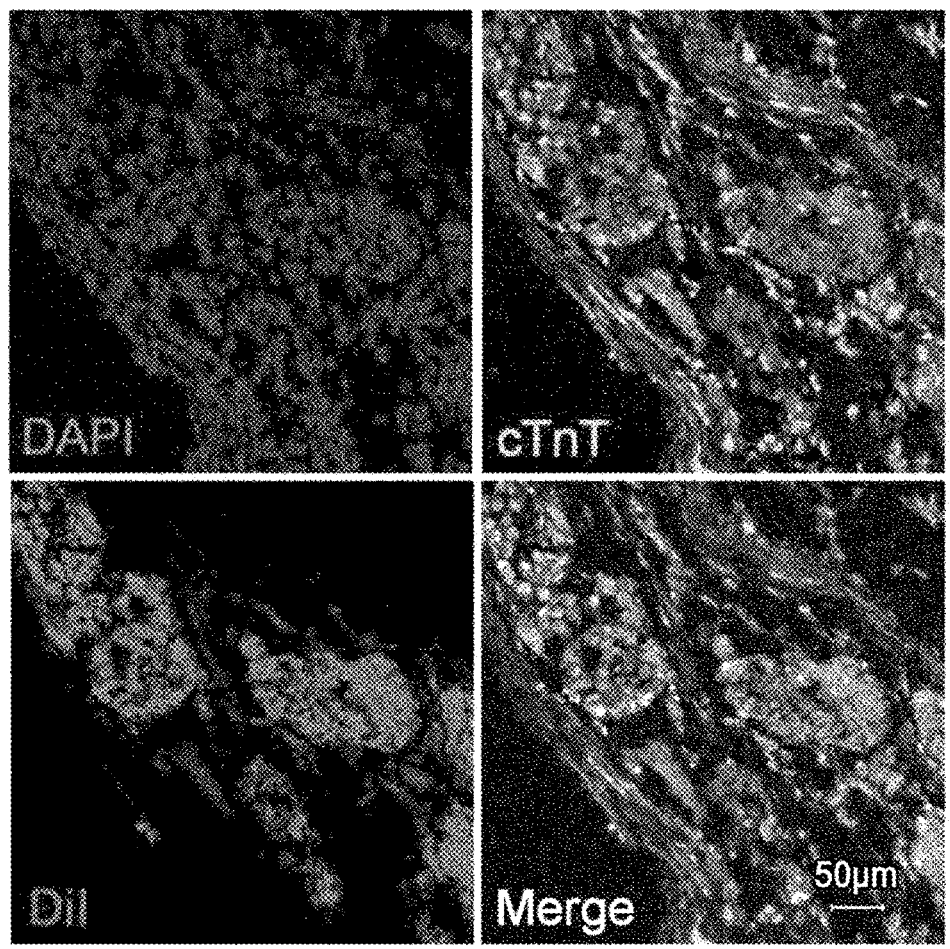

[FIG. 29]
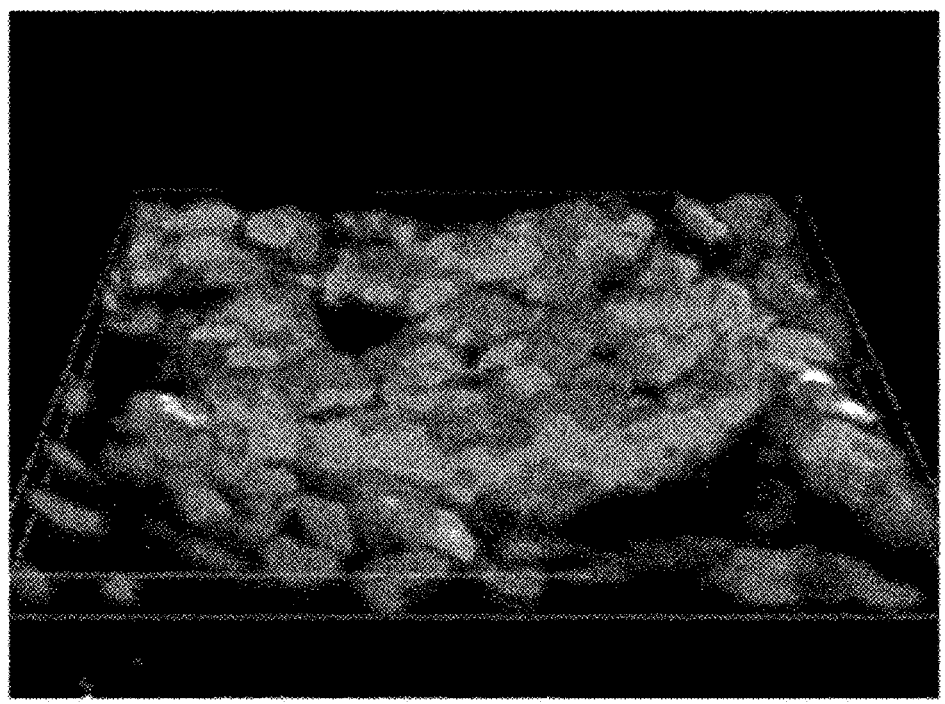

[FIG. 30]
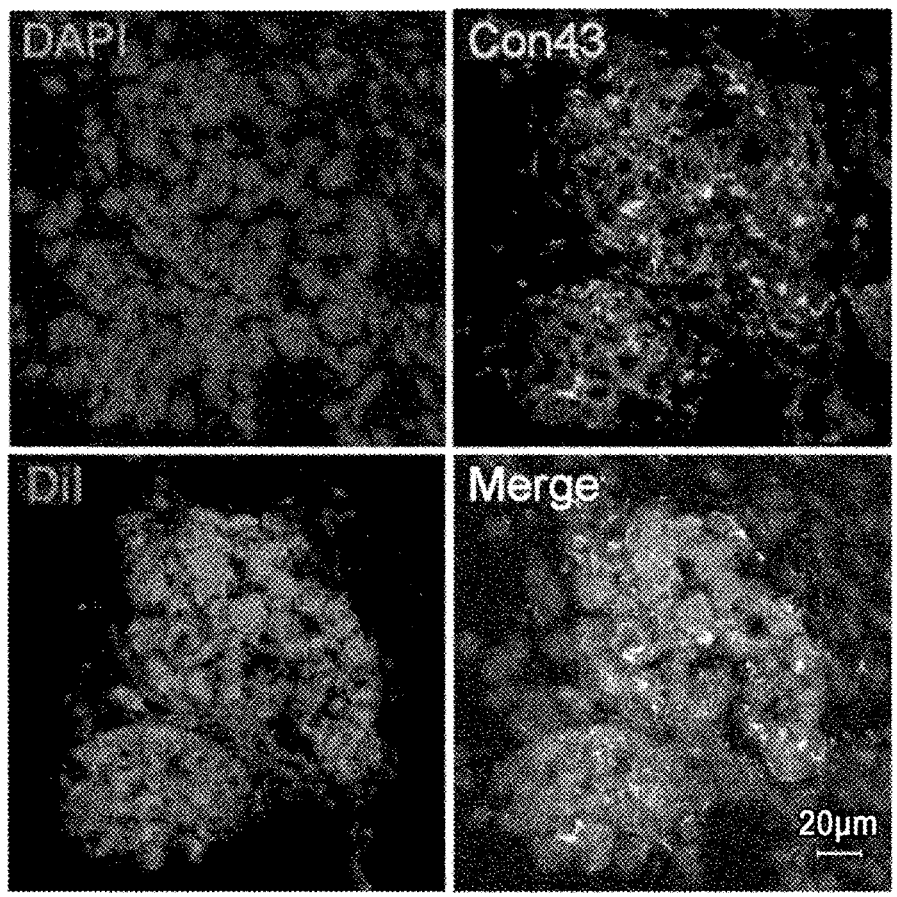
[FIG. 31]
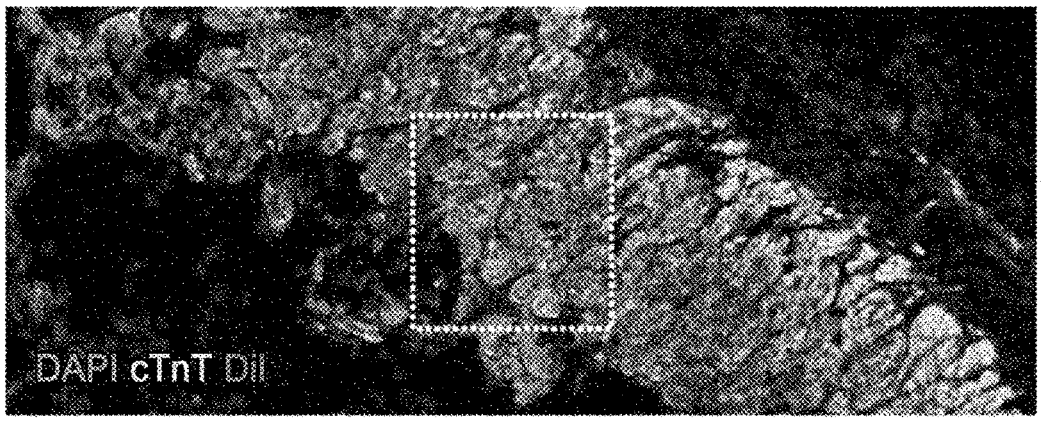

[FIG. 32]
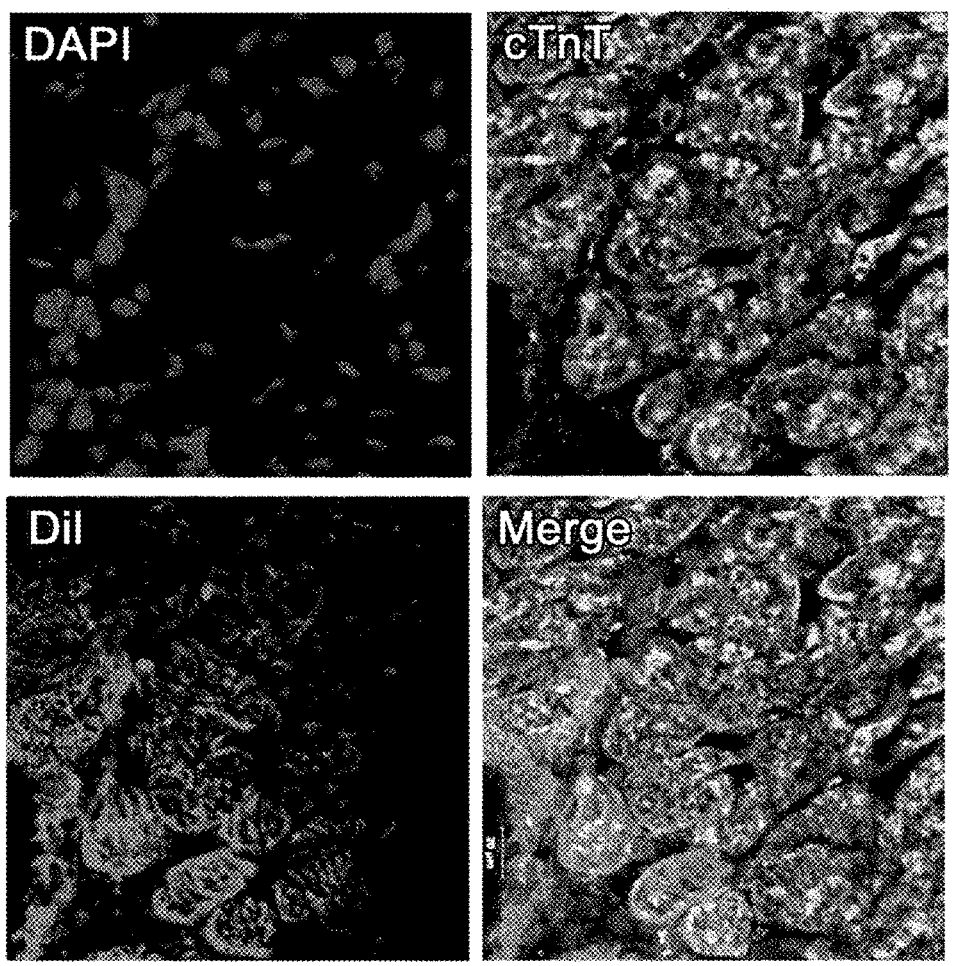

[FIG. 33]
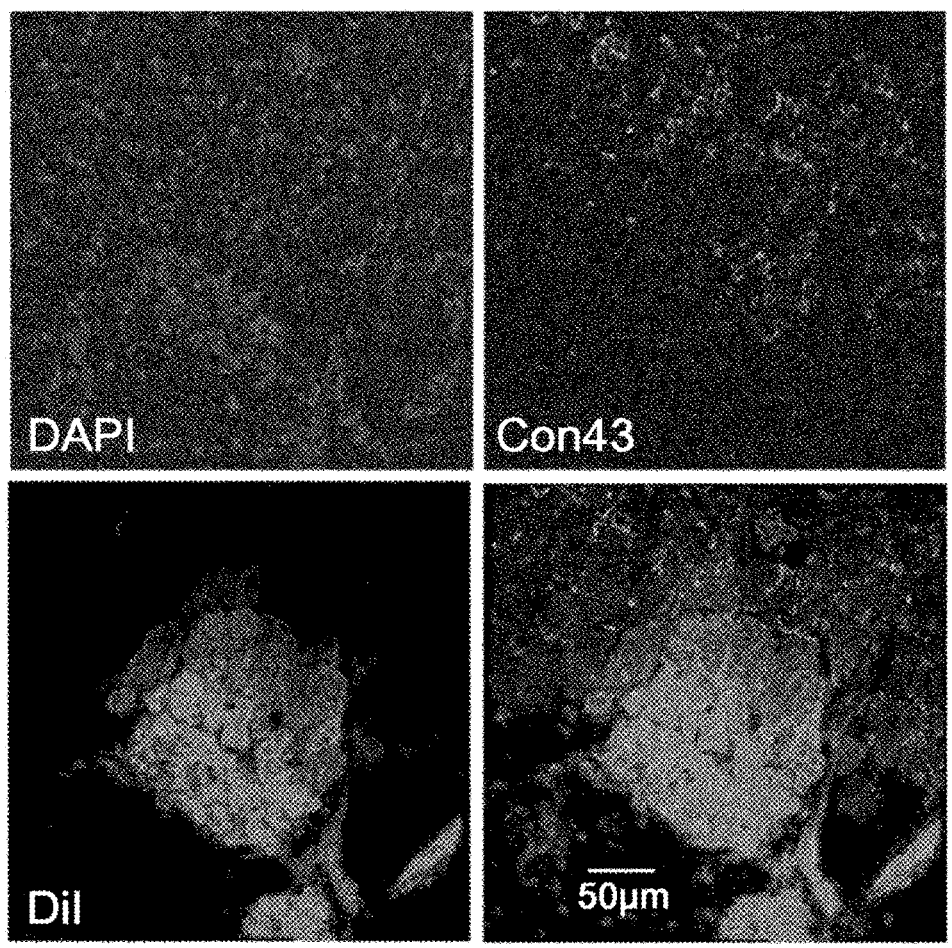

[FIG. 34]
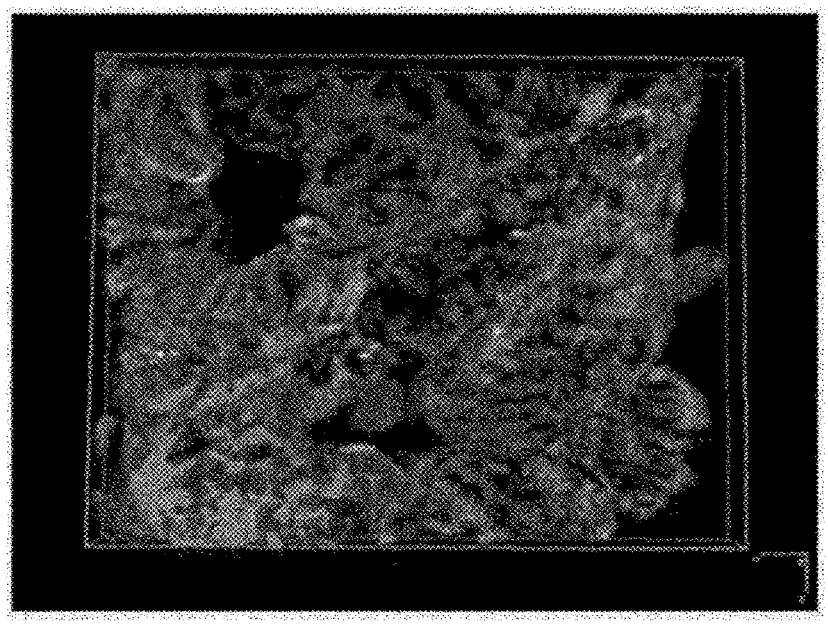

[FIG. 35]
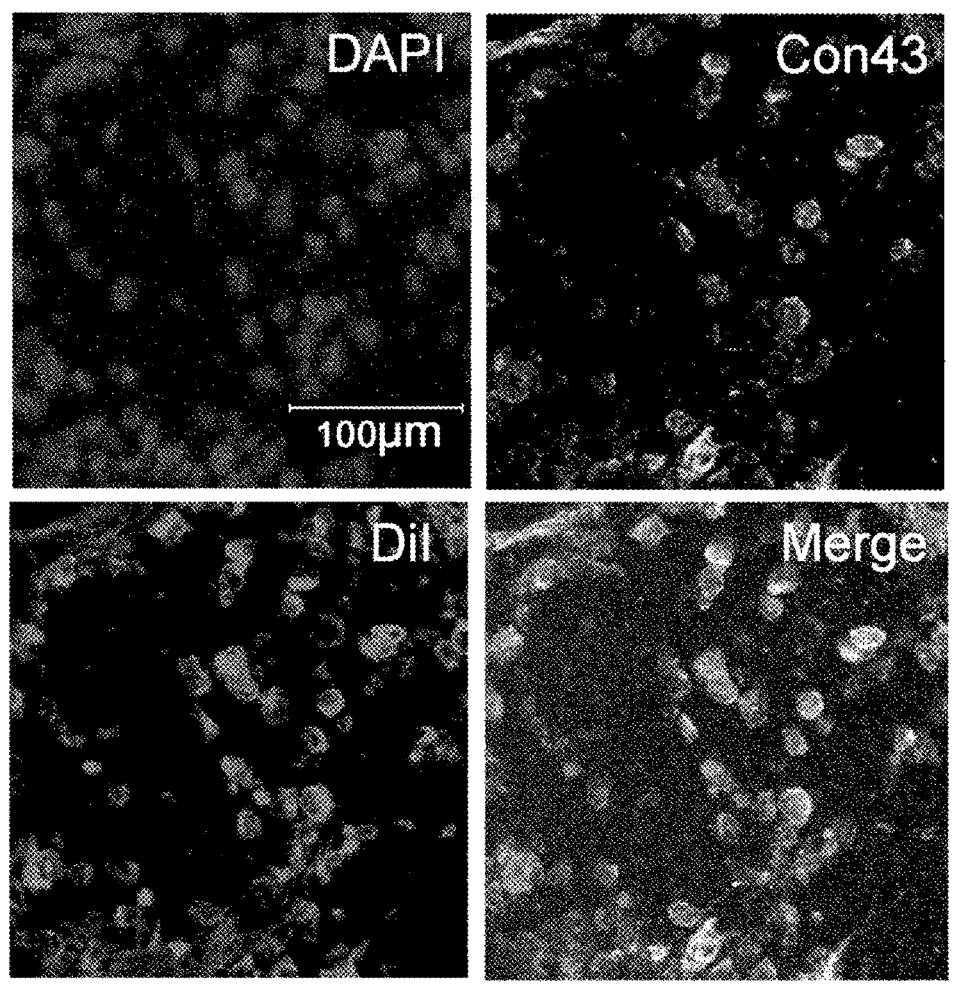

[FIG. 36]
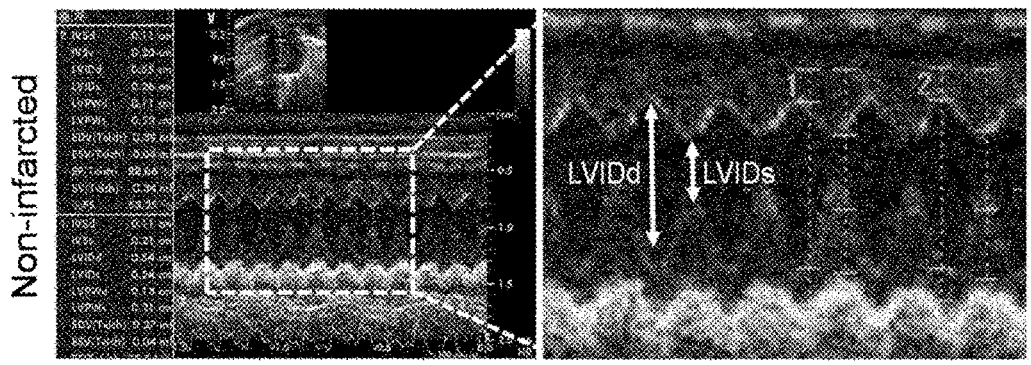
[FIG. 37]
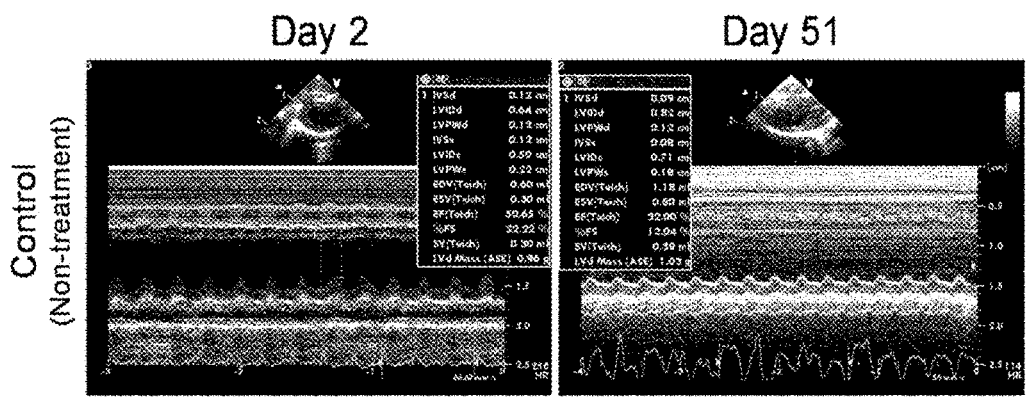
[FIG. 38]
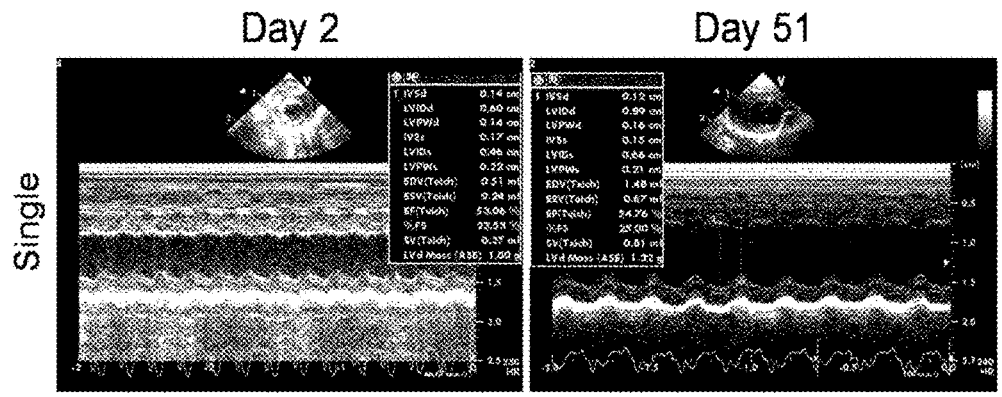

[FIG. 39]
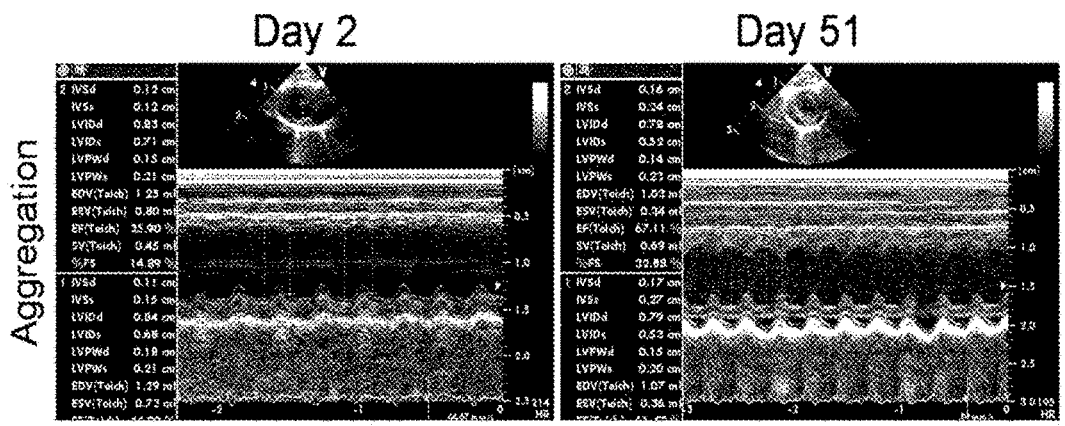

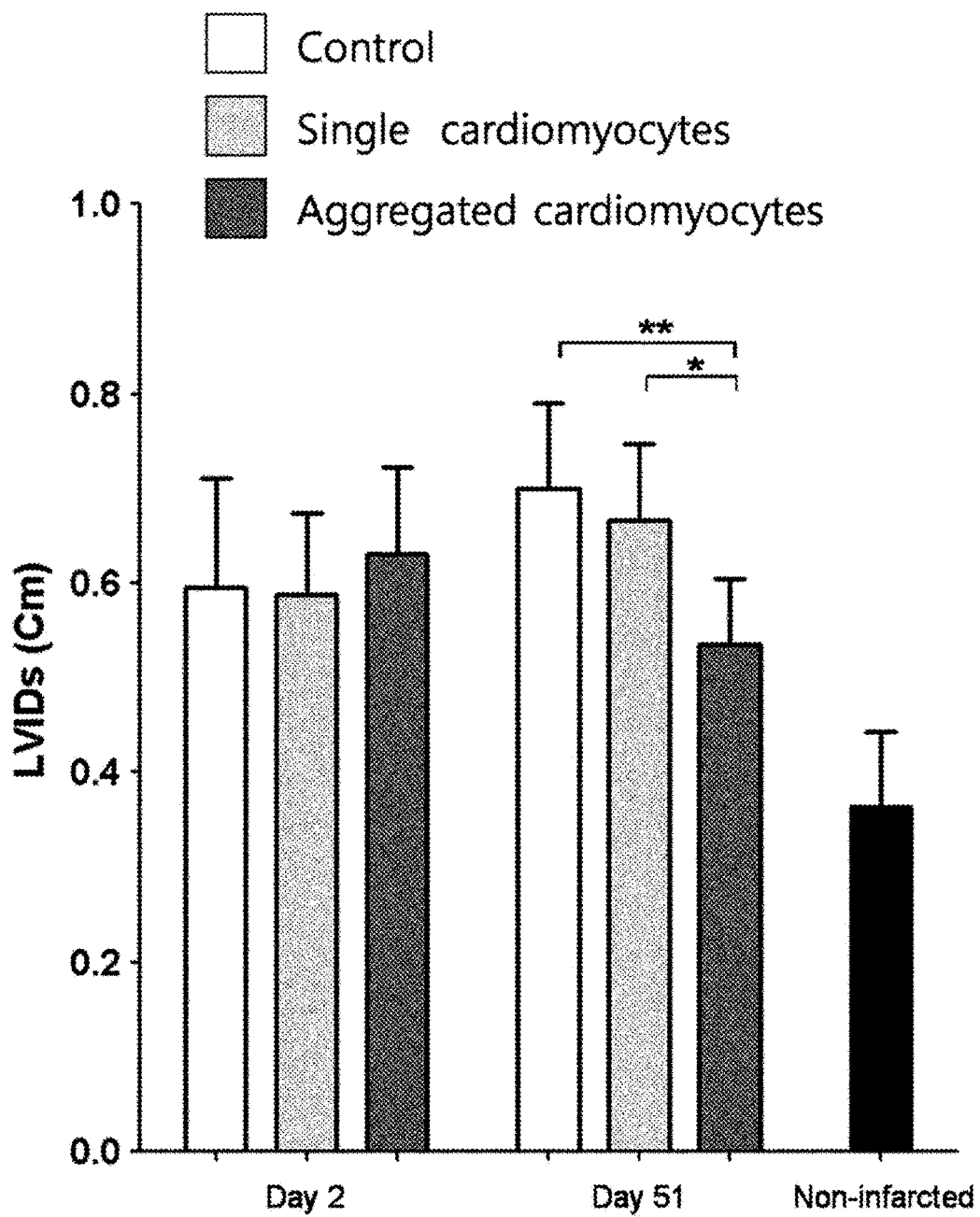
[FIG. 40]

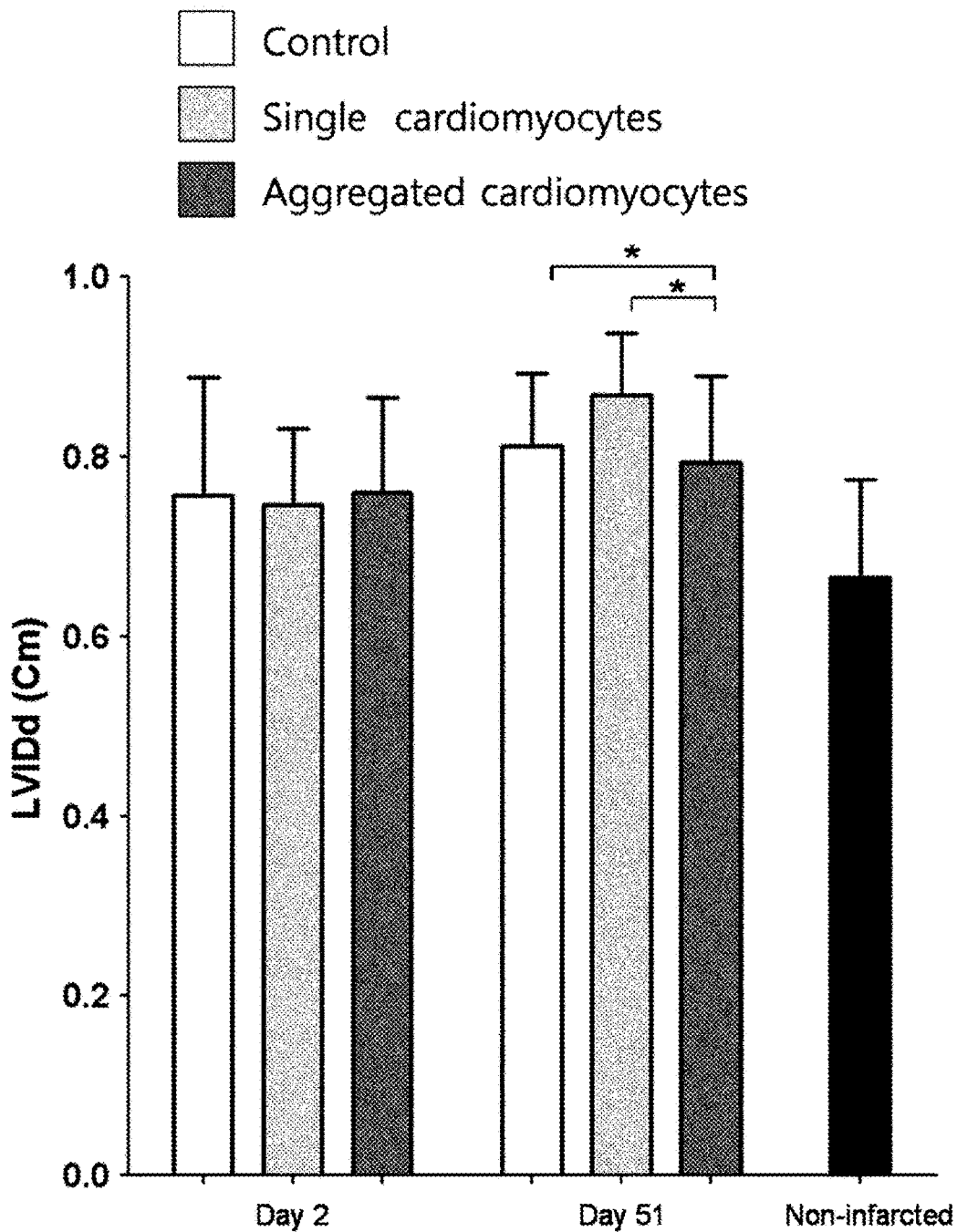

[FIG. 42]
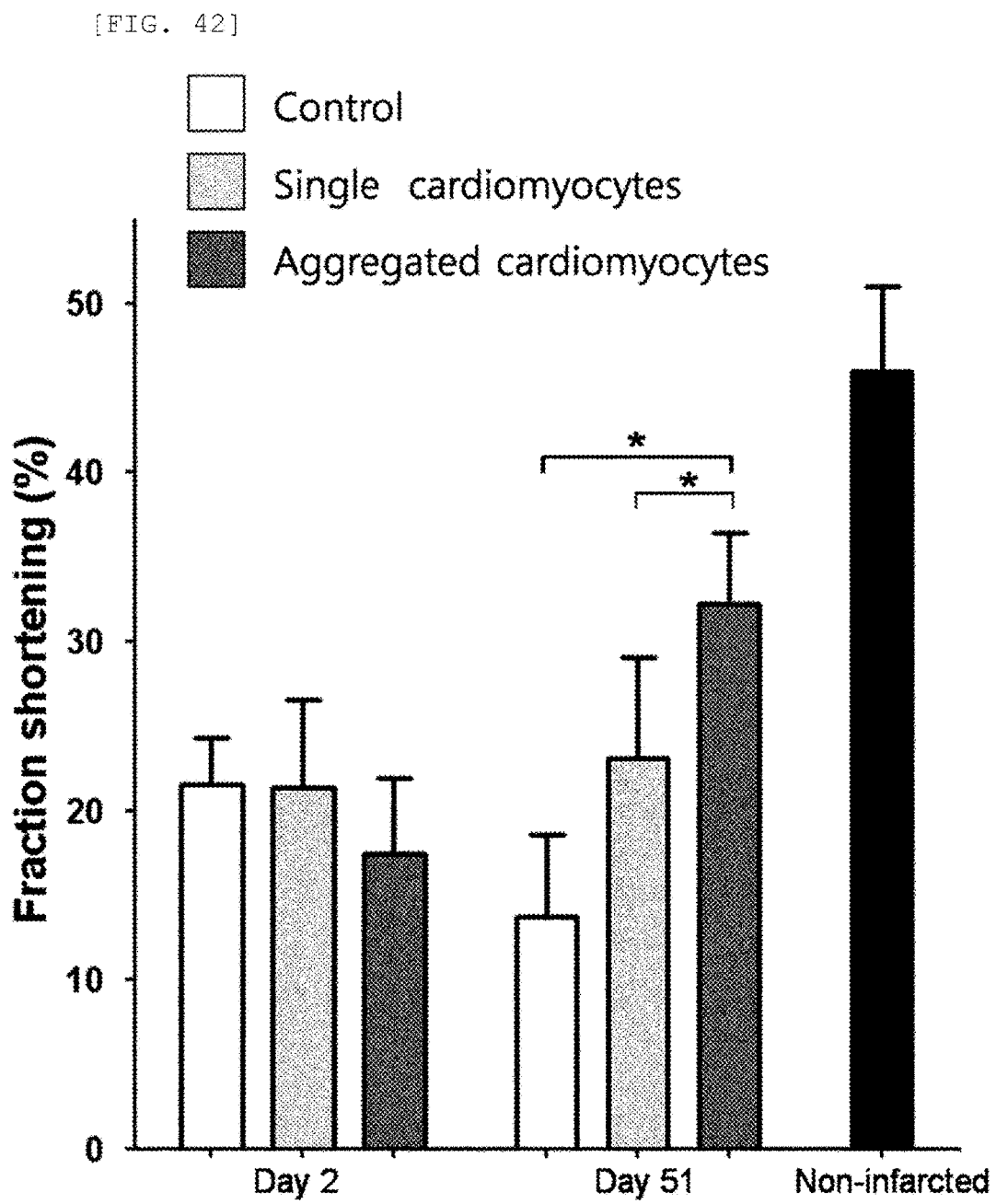

METHOD FOR PRODUCING CARDIOMYOCYTES FROM HUMAN OR MOUSE EMBRYONIC STEM CELLS IN A MEDIUM CONSISTING OF A SERUM-FREE MEDIUM AND N2 SUPPLEMENT

CROSS REFERENCE TO RELATED APPLICATIONS

This application is a continuation of application Ser. No. PCT/KR2011/007408, filed Oct. 6, 2011, which claims priority to Korean Patent Application Ser. No. 10-2010-0097543, filed Oct. 6, 2010. Each of the aforementioned applications is incorporated herein by reference in its entirety.

BACKGROUND OF THE INVENTION

1. Field of the Invention

The present invention relates to embryonic stem cell-derived cardiomyocytes, and a cellular therapeutic agent comprising the same as an active ingredient. More particularly, the present invention relates to a method for producing embryonic stem cell-derived cardiomyocytes, cardiomyocytes produced by the method, a method for producing cardiomyocyte bodies from the cardiomyocytes, cardiomyocyte bodies produced by the method, a cellular therapeutic agent comprising the cardiomyocyte bodies as an active ingredient for the treatment of cardiac diseases, and a method for treating cardiac diseases using the cellular therapeutic agent.

2. Description of the Related Art

Embryonic stem cell (ESC)-derived cardiomyocytes (CM) can be used in regenerative therapies for cardiovascular diseases, and thus a variety of techniques for differentiation and isolation of CMs have been developed by many researchers. However, these methods face difficulties in their practical applications due to a low yield of CMs. CMs have been isolated from contracting human embryoid bodies (hEBs) by microdissection. It has been known that formation of hEBs induces generation of contracting CMs from undifferentiated hESCs, but there are a few drawbacks to CM generation by this method. First, hEBs do not show a unique splitting pattern of three germ layers in three-dimensional culture. Second, the differentiated cells are mixed with cells of different cell lineages. Third, it is difficult to isolate CMs in a high concentration. Therefore, many researchers have tried to isolate a large amount of CMs by mechanical isolation, Percoll density gradient isolation, and by use of KDR, CD15 and CD16.

However, pure CM cells cannot be completely isolated by these methods, and thus there is still a drawback in their clinical application. It is also difficult to apply the conventional culture method in CM isolation due to a lack of CM-specific surface markers. In order to overcome these problems, MLC-2v-induced-GFP-expressing hESCs were produced by transduction using a recombinant lentiviral vector system, and hESCs were used for the isolation of CMs from hEBs by FACS isolation. However, this clinical application of hESCs is highly restricted because viral DNA can be integrated into DNA in the body. In addition, isolation of CMs from contracting hEBs by microdissection has a problem that CMs are mixed with other endodermal lineage cells because of their characteristic of coexisting with endodermal cells rather than ectodermal cells, and many studies have been actively conducted to solve this problem.

On the other hand, it is also an important factor to obtain a sufficient amount of CMs to be used as therapeutic agents for cardiovascular diseases, because mature CMs have limited proliferative activity. For this work, various differentiation methods using growth factors or an END-2 co-culture system with an endodermal cell line providing CM proliferation and differentiation have been developed. However, this method has financially costly due to the use of growth factors, and the inconvenience of further isolating CMs from END-2 cells co-cultured therewith. Accordingly, there is a demand for production and isolation methods of CMs which are able to provide high efficiency and yield for cell-based therapies for cardiac diseases.

Under this background, the present inventors have made many efforts to develop a method for purifying ESC-differentiated cardiomyocytes with high yield and efficiency. As a result, they developed a method for purifying ESC-differentiated cardiomyocytes using a serum-free medium, and found that cardiomyocyte bodies (CBs) to be used for the treatment of cardiac diseases can be produced by suspension-culture of the purified CMs in the serum-free medium, thereby completing the present invention.

SUMMARY OF THE INVENTION

An object of the present invention is to provide a method for producing cardiomyocytes from embryonic stem cells, comprising (a) culturing embryonic stem cells to obtain a culture; and (b) culturing the culture in a serum-free medium to purify cardiomyocytes.

Another object of the present invention is to provide cardiomyocytes produced by the method.

Still another object of the present invention is to provide a method for producing cardiomyocyte bodies, comprising (a) culturing embryonic stem cells to obtain a culture; (b) culturing the culture in a serum-free medium to purify cardiomyoblasts; and (c) culturing the purified cardiomyoblasts in a serum-free medium.

Still another object of the present invention is to provide cardiomyocyte bodies produced by the method.

Still another object of the present invention is to provide a cellular therapeutic agent for treating cardiac diseases, comprising the cardiomyocyte bodies as an active ingredient.

Still another object of the present invention is to provide a method for treating cardiac diseases, comprising the step of administering the cellular therapeutic agent to a subject.

BRIEF DESCRIPTION OF THE DRAWINGS

FIGS. 1 to 4: Cell component analysis of contracting EBs derived from human embryonic stem cells.

(FIG. 1, left panel) Differentiated and contracting EBs derived from human embryonic stem cells appeared when suspension-cultured in a DMEM medium containing 20% FBS for 15 days.

(FIG. 1, middle panel) CM-specific marker cTnT-expressing cells were partially localized as clumps in contracting EBs.

(FIG. 1, right panel) Magnification image of the white box of the second panel.

(FIG. 2, left panel) Contracting and non-contracting areas were isolated on a 0.1% gelatin-coated plate, and thereafter, contracting EBs were plated.

(FIG. 2, middle and right panels) Cells in the contracting cluster area expressed CM-specific markers, cTnT and sMHC.

(FIGS. 3a to 3c) Expression patterns of cardiac lineage-related genes in contracting (1b) and non-contracting areas of EBs. Expressions of the cardiac transcription-related genes (NKX2.5 and MEF-2c) and the CM-related genes (Myh6, Myh7, MLC-2v and TnT) were increased in the contracting area, compared to non-contracting area. Error bars represent mean values of three experiments.

(FIG. 4) Contracting clusters of FIG. 1b were mechanically dissected by 0.05% trypsin-EDTA treatment, and then the cells were re-plated on the 0.1% gelatin-coated plate.

(FIG. 4, left panel) In the re-plated cell populations, contracting cells coexisted with non-contracting cells.

(FIG. 4, middle and right panels) Immunocytochemical analysis showed that contracting cells were positive for the CM-marker, sMHC or cTnT-; in contrast, non-contracting cells expressed no CM marker, but expressed endodermal lineage-specific marker, Foxa2 or AFP.

FIGS. 5 to 11: Effective purification of contracting cells from non-contracting cell populations re-plated on a serum-free medium containing N2, and concentration of ventricular-type CMs.

(FIG. 5, left panel) A majority of cells in a serum-free medium containing N2 showed contractility and strong expression of cTnT (FIG. 5, middle panel) or sMHC (FIG. 5, right panel).

(FIG. 6, left panel) When cells are isolated from contracting clusters cultured in a serum (2% FBS)-containing medium, the present inventors found the co-existence of non-contracting and contracting cells.

(FIG. 6, middle and right panels) Contracting and non-contracting cells in the serum-containing media expressed cTnT and sMHC, respectively.

(FIG. 7) A percentage of CM marker-expressing cells to DAPI-expressing cells on day 14 after culturing isolated cells in a serum-containing or serum-free medium. Error bars represent mean values of five experiments.

(FIGS. 8a to 8c) Expression patterns of cardiac- and endodermal lineage-related genes in the cells cultured under serum-containing and serum-free conditions. Quantitative RT-PCR was performed using cDNAs of the samples and each value was normalized to GAPDH.

(FIGS. 8a and 8b) Under serum-free conditions, expressions of CM-related genes (Myh6, Myh7, MLC-2v and TnT) were increased, and expressions of endodermal lineage-related genes (Foxa2 and AFP) were decreased. The data from the serum-free group was given as a ratio normalized by the serum group. Error bars represent mean values of three experiments.

(FIG. 9) Electrophysiological characterization of CMs derived from human embryonic stem cells. Three main classes of action potentials (nodal-type, atrial-type, and ventricular-type) were recorded from the serum group and the serum-free group. The single action potential was taken from the marked region (*), and shown on an extended time scale. The dotted line represents 0 mV in FIG. 9.

(FIGS. 10 and 11) Ratios of three main classes of action potentials under serum-containing or serum-free culture conditions. The graphs show three main classes of action potentials of H9- and CHA15-human embryonic stem cell-derived cardiomyocytes in the serum-containing or serum-free groups. Of the recorded cells, interestingly, 80% of the cells under the serum-free conditions showed ventricular characteristics.

FIGS. 12 to 16: Enhanced proliferation ability of highly purified CMs in high density culture system.

(FIG. 12) Contractility of low density single cells (left panel) and high density colonized CMs (right panel, ▲) were observed during culture of purified CMs in a serum-free medium containing N2.

(FIG. 13) Contractility comparison over time between single and colonized CMs.

(FIG. 14, left panel) Non-contracting single CMs having surrounding CMs showed expression of a CM-specific marker sMHC (red), but no expression of a proliferation marker Ki-67 (green).

(FIG. 14, right panel) A few colonized CMs showed expressions of Ki-67 as well as sMHC.

(FIG. 15) Quantification of Ki-67-expressing cells in DAPI-expressing cells showed that colonized CMs had a higher ratio of Ki-67-expressing cells than single CMs. Error bars represent standard deviations from three experiments.

(FIG. 16) Measurement of 6-week CM proliferation rate under low- and high-density conditions.

FIGS. 17 to 23: Colonization of purified human embryonic stem cell-derived CMs.

(FIG. 17) Contraction of single CMs under suspension conditions.

(FIG. 18) CM bodies were formed when $5\times10^3$ of single contracting CMs were aggregated in 20 μl overnight, and then cultured under suspension-culture conditions using a serum-free medium containing N2 on an ultra-low attachment culture dish for 7 days.

(FIG. 19) All cells in synchronized beating clusters were cTnT-positive.

(FIG. 20) Co-expression of cardiac-specific transcription factor Nkx2.5 (green) with DAPI (red) was found in the nuclei of all cells of clusters. The cardiac-specific gap junction marker Con43 (red) was also expressed in the cell membrane of cell to cell interaction zone inside the cluster.

(FIG. 21) Sarcoma structure was clearly observed by sMHC staining in synchronized clusters.

(FIG. 22) After myocardial infarction in the rat heart, cardiomyocyte bodies were transplanted into two zones of the ischemic heart using a 10 μl micropipette.

(FIG. 23) Functional study (FS) of LV by echocardiography.

FIGS. 24 to 34: Histological studies of the graft at 7 weeks after the surgery of myocardial infarction.

(FIG. 24) Hematoxylin-eosin staining.

(FIG. 24, ←) Magnification image of injected cells in cardiomyocyte bodies transplantation, which was not detected in the single cell transplantation (FIG. 24, Δ).

(FIG. 25) Masson's trichrome staining shows the left ventricle fibrosis by the surgery of myocardial infarction.

(FIG. 25, ←) Magnification image of fibrosis inhibition by transplanted cardiomyocyte bodies in infracted zone, which was not detected in single-cell transplantation (FIG. 25, Δ)

(FIG. 26) Staining for cTnT.

(FIG. 26, ▲) Non-detection of injected DiI-labeled cell clusters.

(FIG. 26, ←) Strong expression of DiI-labeled graft in infracted zone in transplanted area showed survival of transplanted cardiomyocyte bodies.

(FIG. 27) Analysis of transplanted cardiomyocyte bodies in external (←) and internal (▲) areas of the boundary zone.

(FIGS. 28 to 30) Immunohistochemical analysis of the graft in the external area (FIG. 27, ▲) of the ischemic heart.

(FIG. 28) DiI-labeled graft co-expressed cTnT.

(FIG. 29) Structure of DiI and cTnT co-expressing area by 3-Dimensional imaging.

(FIG. 30) Con43 was specifically expressed in the DiI-labeled graft, but not in the host zone.

(FIGS. 31 to 32) Immunohistochemical analysis of the graft in the internal area (FIG. 27, ▲) of the ischemic heart.

(FIG. 31) DiI-expressing graft to the host zone observed in the internal area of the ischemic heart.

(FIG. 32) Magnification image of the white box of FIG. 31.

(FIG. 33) Grafts stained with Con43 antibodies in the internal area of the ischemic heart and DiI-expressing cells in the migrated area from the host.

(FIG. 34) Magnification image of FIG. 33.

FIG. 35: Histological evaluation of single CM transplantation. Gap junction expression of transplanted CMs in the internal area of serially sectioned tissue. A majority of DiI-labeled cells co-expressed the gap junction-specific marker Con43 (green) in the internal area of the ischemic heart, but there was no contact with the host, unlike cardiomyocyte bodies transplantation.

FIGS. 36 to 42: Echocardiography of infarcted left ventricle transplanted with CMs derived from human embryonic stem cells.

(FIG. 36) M-mode echocardiograms of non-infarcted rat heart.

(FIGS. 37 to 39) M-mode echocardiograms of each group on days 2 (left panel) and 51 (right panel).

(FIGS. 40 to 42) Analysis of left-ventricular internal diastolic dimension (LVIDd), left-ventricular internal dimension in systole (LVIDs) and fractional shortening (FS) on days 2 and 51.

DETAILED DESCRIPTION OF THE PREFERRED EMBODIMENTS

In one aspect to achieve the above objects, the present invention provides a method for producing cardiomyocytes from embryonic stem cells using a serum-free medium. Specifically, the method for producing cardiomyocytes comprises the steps of (a) culturing embryonic stem cells to obtain a culture; and (b) culturing the culture in the serum-free medium to purify cardiomyocytes.

As used herein, the term "cardiomyocyte (CM)" generally refers to a cell constituting the myocardium which is the middle layer of the cardiac wall, and with respect to the objects of the present invention, the cardiomyocytes comprise any cells at any differentiation stage without limitation, such as cardiomyoblasts which are differentiated from embryonic stem cell to form sarcomeres, cardiomyocyte progenitor cells which have a potential to be functional cardiomyocytes, e.g., cardiomyocytes differentiated from cardiomyoblasts, fetal cardiomyocytes, and adult cardiomyocytes, and the cardiomyocyte refers to a cell that can be identified by at least one of the methods listed below, preferably by at least one of the multiple methods, and more preferably by multiple markers or criteria.

Expressions of various cardiomyocyte-specific markers can be detected by the known biochemical or immunochemical methods, and these methods can be used without limitation. In the methods, marker-specific polyclonal antibodies or monoclonal antibodies binding to cardiomyocyte progenitor cells or cardiomyocytes can be used. The antibodies targeting each of the specific markers may be commercially available or prepared by the known method without limitation. The markers specific to cardiomyocyte progenitor cells or cardiomyocytes may comprise, but are not limited to, α-actinin, troponin I (cTn I), ANP, GATA4, Nkx2.5, MEF-2c, MYH6, MYH7, Con43, myosin heavy chain (α-MHC or sMHC), myosin light chain (MLC-2α or MLC-2v), cardiac actin, cTnT, cTnI, and preferably cTnT and sMHC.

In addition, expressions of the markers may be detected by the common molecular biological methods used for amplifying, detecting, translating mRNA encoding any marker protein, such as reverse transcriptase-polymerase chain reaction (RT-PCR) or hybridization assay, but are not limited to a particular method. The nucleic acid sequences encoding the markers are already known and thus can be obtained from public databases such as GenBank. Marker specific sequences needed to be used as primers or probes can be easily determined. In addition, physiological criteria can be further used to detect differentiation of multipotent cells into cardiomyocytes. That is, spontaneous pulsatile beating, or expression of various ion channels and response to electrical stimulation can be also utilized as an index for detecting differentiation of cardiomyocytes from multipotent cells.

As used herein the term "embryonic stem cells" refers to cells, extracted from the inner cell mass of blastocysts at a stage just before implantation in the mother's uterine and cultured ex vivo, having pluripotency, which are able to differentiate into any cell type of the human body. The embryonic stem cells used in the present invention are, but not particularly limited to, preferably human embryonic stem cells or mouse embryonic stem cells, of which production methods and characteristics have been established. The culture obtained by culturing the human embryonic stem cells may comprise, but is not particularly limited to, embryoid bodies containing all of ectodermal cells, mesodermal cells, and endodermal cells that are differentiated from embryonic stem cells, preferably endodermal cells and mesodermal cells, and more preferably, endodermal cells and CM.

The embryoid bodies may comprise CMs differentiated from embryonic stem cells, and show contractility due to the comprised CMs. The content of CMs in the embryoid bodies may be approximately 10 to 15%, but is not particularly limited thereto.

The embryonic stem cells may be those pre-cultured on a mitotically inactive mouse embryonic fibroblast (MEF) feeder layer using a serum-containing culture medium for stem cells, and upon the following suspension-culture, embryonic stem cells isolated from the feeder layer may be used.

The serum-containing culture medium for stem cells may be, but is not particularly limited to, preferably a hESC medium (containing L-glutamine, non-essential amino acids, beta-mercaptoethanol and bFGF) supplemented with serum or serum alternative, and the content of serum or serum alternative is, but not particularly limited to, preferably 10 to 20% (v/v).

As used herein, the term "suspension culture", also called floating culture, refers to cells that are suspended or floating in a liquid medium in a culture vessel, and in order to maintain the cells in the suspension or floating state, the medium should be stirred during culture. The suspension culture may be carried out for the purposes of purifying CMs and of generating a culture, preferably, contracting embryoid bodies from embryonic stem cells.

The suspension culture for producing the culture may be carried out by a primary culture of the embryonic stem cells in a bFGF-removed basal hESC medium and by a secondary culture in a medium containing serum or serum alternative. The basal hESC medium is, as described, a medium containing L-glutamine, non-essential amino acids, beta-mercaptoethanol and bFGF, and the medium containing serum or serum alternative may be, but is not particularly limited to, preferably a basal hESC medium containing serum such as FBS, and the content of serum or serum alternative in the medium is, but is not particularly limited to, preferably 10 to 20% (v/v).

Meanwhile, the suspension culture for purifying CMs may be carried out so that the culture, preferably, the contracting embryoid body is cultured in a serum-free medium to kill cells other than CMs and allow for the survival of only CMs, thereby achieving the effect of purifying CMs.

As used herein, the term "serum-free medium" refers to any cell culture medium containing no heterologous or homologous serum, and any cell culture medium known in the art may be used as long as it contains no serum.

A serum-containing medium is typically needed for culturing mature differentiated cells. However, the present invention revealed that CMs survive, but other cells do not in the serum-free medium.

Further, the risk of contamination that may occur in clinical application due to pollutants comprising mad cow disease virus from cow-derived substances such as fetal bovine serum (FBS) or bovine serum (FCS) present in the serum medium can be eliminated by the use of serum-free medium.

Further, the risk of transplant rejection of transplanted cells caused by the induction of antibody formation by the proteins in the serum can be eliminated by the use of serum-free medium, so that the cardiomyocytes produced by the method of the present invention can be applied in cell therapies for cardiac-related diseases without clinical risk.

The serum-free medium may be, but is not particularly limited to, preferably a medium containing no other growth factors, serum or serum alternative but containing insulin, human transferrin, progesterone, putrascine and selenite, more preferably a medium containing N2 supplement, and most preferably a DMEM medium containing N2 supplement.

The serum-free medium, preferably the medium containing insulin, human transferrin, progesterone, putrascine and selenite, more preferably the medium containing N2 supplement, and much more preferably the DMEM medium containing N2 supplement do not contain essential components for growth, differentiation, and proliferation of cells derived from embryonic stem cells so as to provide harsh environments during cell culture, and thus cells in need of growth, differentiation, and proliferation cannot survive in the media. On the contrary, differentiation-terminated CMs are not needed to undergo cell growth, differentiation, proliferation owing to their nature, and thus are able to sufficiently survive under the harsh environments provided by the media. Consequently, the media show inhibitory effects on the survival of various types of differentiated cells other than CMs, and ultimately, CMs can be purified from the culture.

In order to improve the efficiency of purifying CMs from the culture, if necessary, a isolation step at a cellular level may be further performed prior to the suspension culture. The isolation at a cellular level may be performed preferably using a proteolytic enzyme, and more preferably using trypsin but is not particularly limited to the above methods. When the isolation at the cellular level is performed, all of the individual cells isolated from the culture are directly affected by serum-free medium, thereby purifying CMs more quickly and effectively.

According to one embodiment of the present invention, the present inventors have found that three-dimensional aggregates, embryoid bodies (EBs) are formed from human embryonic stem cells (hESCs) in vitro (FIG. 1), and contracting cardiomyocytes (CMs) comprised therein were identified by immunocytochemical analysis (FIG. 1). The EBs were found to have an area showing contractility and expression of CM-specific markers, cTnT and sMHC and an area showing no contractility and no CM-specific marker expression (FIG. 2). Expressions of the cardiac-related transcription factors (NKX2.5 and MEF-2c) and the cardiac-specific, sarcomeric protein-encoding genes (MLC-2v, MYH6, MYH7, and TnT) were observed in the EB area showing contractility and expression of CM-specific markers cTnT and sMHC (FIG. 3). Further, expressions of the endodermal markers, FoxA2 and AFP were observed in the EB area showing no contractility and no CM-specific marker expression (FIG. 4). These results suggest that it is necessary to purify cardiomyoblasts from EBs for the preparation of CMs from hESCs.

Therefore, the present inventors intended to produce cardiomyocytes from embryonic stem cells by purifying CMs from the embryoid bodies. To achieve this, the present inventors produced cardiomyocytes from embryonic stem cells by culturing embryonic stem cells to obtain a culture, and then by culturing the culture in the serum-free medium to purify cardiomyocytes. In detail, the present inventors cultured embryoid bodies using the DMEM medium containing N2 supplement (Experimental group), and cultured embryoid bodies using the DMEM medium containing serum and N2 supplement as a control group. As a result, the number of cells cultured in the experimental group was similar to that of the control group, and the contracting cells were also observed in both the experimental group and the control group, but non-contracting cells were observed not in the experimental group but in the control group (FIGS. 5 and 6). The result of immunocytochemical analysis using the CM-specific markers cTnT and sMHC showed that the CM-specific markers cTnT and sMHC were expressed in most cells of the experimental group (80% or above), but the CM-specific markers cTnT and sMHC were expressed in 50% or fewer cells of the control group (FIG. 7). Furthermore, gene expression levels of the cardiac-specific markers cTnT, Myh6, Myh7 and MLC-2v and the endodermal markers FOXA2 and AFP in the cells of the experimental group and the control group were determined by qRT-PCR and compared to each other. As a result, the cells of the experimental group showed high expression levels of the cardiac-specific markers, but low expression levels of the endodermal lineage markers (FIG. 8). Finally, to provide initial functional evaluation of hESC-derived CMs, whole-cell patch clamp recording of the contracting cells was performed. The result showed that the ventricular-type action potential was remarkably increased in the cells of the experimental group, compared to the control group (FIGS. 9 and 10).

In another aspect, the present invention provides cardiomyocytes produced by the above method. The cardiomyocytes has the following characteristics of:

(i) expressing a marker selected from the group consisting of α-actinin, troponin I (cTn I), ANP, GATA4, Nkx2.5, MEF-2c, MYH6, MYH7, Con43, myosin heavy chain (α-MHC or sMHC), myosin light chain (MLC-2α or MLC-2v), cardiac actin, cTnT and cTnI;

(ii) having a cyst-like shape, a mixed shape, a floating or muscle-like shape; and (iii) showing pulsatile beating.

In still another aspect, the present invention provides a method for producing cardiomyocyte bodies (CBs) from the cardiomyocytes. Specifically, the method for producing cardiomyocyte bodies of the present invention comprise the steps of (a) culturing embryonic stem cells to obtain a culture; (b) culturing the culture in a serum-free medium to purify cardiomyoblasts; and (c) culturing the cardiomyoblasts in a serum-free medium. In this regard, the culture may be carried out in a method identical to that of the suspension culture in the purification process of CMs, but is not particularly limited to the above process, and the serum-free medium used for culture may be, as described above, the medium containing no other growth factors, serum or serum alternative but containing insulin, human transferrin, progesterone, putrascine and selenite, more preferably the medium containing N2 supplement, and most preferably the DMEM medium containing N2 supplement.

In still another aspect, the present invention provides cardiomyocyte bodies (CBs) produced by the above method. The CBs produced by the above method may show synchronized beating and have a diameter of 200 to 500 μm.

As used herein, the term "cardiomyocyte bodies (CBs)" refer to CM aggregates that are formed by suspension-culturing the purified hESC-differentiated CMs for a long period of time under the conditions devoid of components essential for growth, differentiation, and proliferation of cells. Preferably, the CBs of the present invention may show synchronized beating, and their size may be, but is not particularly limited to, preferably a diameter of 200 to 500 μm. The CB is a type of tissue resulting from high density aggregation of CMs to adapt the harsh culture environments. Because CB shows synchronized beating, it can be transplanted for cardiac diseases, in terms of its contractility as well as density.

According to one embodiment of the present invention, the present inventors produced CM bodies (cardiomyocyte bodies, CBs), and they demonstrated their effect by transplantation into the myocardial infarction-induced heart. In detail, the purified hESC-derived CMs were suspension-cultured for 7 days by a hanging drop method so as to produce CBs having a diameter of 200 to 500 μm (FIG. 17). The produced CBs showed synchronized beating (FIG. 18). For characterization of the produced CBs, immunocytochemical analysis was performed using the cardiac-specific markers cTnT, Nkx2.5, Con43 and sMHC, and the result showed expressions of the cardiac-specific markers (FIGS. 19 to 21). Meanwhile, CMs were transplanted into the cardiac lesions of myocardial infarction-induced animal model in the form of CBs, and after a period of time, the transplanted area was histologically analyzed. The result showed that no teratoma formation was detected in the transplanted tissue, indicating that the cells have no differentiation capability, because the teratomas are formed upon transplantation of stem cells having differentiation capability. In addition, when CMs were transplanted in the form of CBs rather than single cells, more extensive tissue regeneration was observed (FIG. 24), less fibrous tissue was observed (FIG. 25), bulky cardiac muscle tissue was detected (FIG. 26), and cardiac muscle regeneration was induced by transplantation of CBs into the infarct (FIGS. 27 to 34). In particular, compared to the transplantation of single CM cells, transplantation of CBs showed the extensive presence of DiI-positive cells (FIGS. 28 and 29), and Con43-positive cells localized in the DiI-positive cell-detected area (FIG. 30). A few sporadic transplants were observed between transplanted CBs and single cells in the boundary zone (FIGS. 31 to 34). However, engraftment of DiI-positive cells or Con43 was not observed in the control group transplanted with single CM cells (FIG. 35). Therefore, the effect of CB transplantation on left-ventricular (LV) function was examined. As a result, significant increased LVIDs values were observed in rats transplanted with single CM cells, whereas reduced LVIDs values were observed in rats transplanted with CBs (FIG. 40). On day 51 after transplantation, LVIDd values mostly increased, compared to those measured on day 2. The rats transplanted with CBs showed the lowest increase level of LVIDd, compared to non-transplanted rats or rats transplanted with single CM cells (FIG. 41), and the rats transplanted with CBs showed significantly increased fractional shortening values, compared to non-transplanted rats or rats transplanted with single cells (FIG. 42).

In still another aspect, the present invention provides a cellular therapeutic agent for the treatment of cardiac diseases, comprising the cardiomyocyte bodies of the present invention as an active ingredient.

As described above, CBs showing synchronized beating is able to exhibit normal cardiac functions when transplanted into the heart of a patient with cardiac diseases, and thus can be used as an active ingredient of a cellular therapeutic agent for cardiac diseases. The CBs showing synchronized beating can be easily obtained by the production method of the present invention.

As used herein, the term "cellular therapeutic agent" refers to a drug used for the purpose of treatment, diagnosis and prevention, which contains a cell or tissue prepared through isolation from humans, culture and specific operation (as provided by the US FDA). Specifically, it refers to a drug used for the purpose of treatment, diagnosis and prevention through a series of behaviors of in vitro multiplying and sorting living autologous, allogenic and xenogenic cells or changing the biological characteristics of cells by other means for recovering the functions of cells or tissues. With respect to the objects of the present invention, the CBs showing synchronized beating can be used in a variety of therapeutic protocols for enhancement, treatment or substitution through engraftment, transplantation, or injection into the cardiac tissues, and they substitute or strengthen the cardiac tissues to be a new or altered tissue or to bind with a biological tissue or structure.

In still another aspect, the present invention provides a method for treating cardiac diseases using the cellular therapeutic agent of the present invention. Specifically, the method for treating cardiac diseases of the present invention comprises the step of administering the CBs or the cellular therapeutic agent to the heart of a subject in need of treatment of cardiac diseases.

As used herein, the term "subject" refers to an animal comprising human with cardiac diseases or with the possibility of cardiac diseases.

The cellular therapeutic agent may be administered via any of the common routes, as long as it is able to reach a desired tissue. In addition, the cellular therapeutic agent may be administered by any device capable of delivering the active ingredient to the target cell.

The cellular therapeutic agent of the present invention may be administered in a therapeutically effective amount, and as used herein, the phrase "therapeutically effective amount" refers to an amount sufficient to treat the disease at a reasonable benefit/risk ratio applicable to any medical treatment. An effective dose level may vary depending on a variety of factors comprising the type, severity, age, and sex of the subject, drug activity, drug sensitivity, administration time, administration route, discharge ratio, treatment period, and co-administered drugs, and other factors well known in the medical field. The cellular therapeutic agent of the present invention may be administered alone or in combination with other therapeutics. The co-administration of the agent of the present invention with other therapeutics may be carried out simultaneously or sequentially. Single or multiple dosages are possible. It is important to use the agent in the minimum possible amount sufficient to obtain the greatest therapeutic effect without side effects, considering all the factors.

Typically, when related diseases are treated using the cellular therapeutic agent comprising undifferentiated stem cells or stem cell-differentiated cells as an active ingredient, the cellular therapeutic agents are isolated depending on the type of cells, and then administered into the lesion of the subject via a syringe. The reason of isolating the cellular therapeutic agents depending on the type of cell is to prevent a reduction in the effects of cellular therapeutic agent due to co-administered cells, in addition to convenient injection via the syringe.

Unlike the typical method for using the cellular therapeutic agent, the cellular therapeutic agent of the present invention can be used by directly transplanting the active ingredient cardiomyocyte bodies into a cardiac lesion of the subject in need of treatment. As described above, because the cardiomyocyte bodies of the present invention show synchronized beating, cardiac diseases can be more effectively treated by the use of cardiomyocyte bodies than the use of single contracting cardiomyocytes. The present inventor have demonstrated for the first time that cardiac diseases can be more effectively treated by using cardiomyocyte bodies showing synchronized beating. The cardiomyocyte bodies showing synchronized beating can be easily obtained by the method for producing cardiomyocyte bodies of the present invention without an additional apparatus.

Human embryonic stem cells are a promising source of cardiomyocytes for treating cardiac diseases. Previous studies showed that transplantation of human embryonic stem cells regenerates cardiac tissues and improves contraction of infarcted heart. However, injection of undifferentiated human embryonic stem cells and non-targeted cells derived from undifferentiated human embryonic stem cells into the myocardium leads to undesirable teratoma formation or non-targeted tissue formation in the subject. In addition, transplantation of completely differentiated cardiomyocytes causes the unfavorable survival and engraftment. In order to overcome these problems, the present inventors have developed a purification method for producing pure CMs from human embryonic stem cells and a transplantation method for improving cell survival and engraftment in the infarcted heart. In the present invention, the present inventors selected differentiated CMs using the serum-free medium and excluded other lineage cells from contracting EBs. A defined serum-free medium allows only contracting CMs to survive and to maintain their functions. This method produced considerably pure CMs derived from contracting EBs, which maintain contractility and express CM-related markers in the defined serum-free medium.

There are various approaches for purifying hESC-derived CMs; selection of spontaneously contracting CMs obtained by mechanical dissection after EB formation as the typical method of purifying CMs from human embryonic stem cells; physical isolation such as Percoll density gradient centrifugation; or selection of cell surface markers such as fluorescence-activated cell sorting. These purification methods require much cost and labor. Therefore, efficiency of these methods depends on specialized instruments and skills. However, the method for purifying cardiomyocytes of the present invention provides a simpler procedure without need of any specialized instruments and skills. Moreover, this method does not require genetic modification of cells. Genetic modification using a non-viral or viral system has the disadvantages of foreign gene expression, difficulties of gene expression control, and possibilities of tumorigenesis. In addition, a serum containing many non-specialized factors that exert unknown functions in cell growth and differentiation is not used in the present invention. In clinical applications, the use of serum-free medium can reduce a potential risk of pathogen contamination.

On the other hand, drug development is aimed to develop medicines directly applied to humans, and therefore, it is preferable that the activity of the drug is tested by applying the drug to human-derived cells having characteristics similar to humans. For this reason, of the cells developed for drug testing, embryonic stem cells or induced pluripotent stem cells are expected to be the most useful tools for drug development. Theoretically, these cells could differentiate into many different types of cells constituting the body, and therefore, these cells are expected to be a source of cells targeted by compounds needed for drug development and a source for mass-production owing to their nature of unlimited proliferation. For this work, techniques of applying stem cells in drug development have been actively studied, and stem cells resulting from these studies have application in all stages of drug development, from the initial stage to the preclinical stage, comprising disease etiology study, discovery of new drug target, secondary pharmacology, safety pharmacology, metabolic profiling and toxicity evaluation.

For low failure rate and high profitability in the drug development stage, in vitro evaluation using normal human cells should be performed. However, since in vitro culture of human normal cells causes loss of intrinsic ability of human cells, primary culture cells or tumor cell lines have been mainly used. Cardiotoxicity accounts for the most importance of in vitro evaluation. The cardiotoxicity is caused by complex reactions such as multiple ion channels and change in intracellular ion concentration, and thus the accuracy of evaluation is as high as possible. For this reason, it is essential to test cardiotoxicity by in vitro evaluation, but there is a difficulty in obtaining cardiac cells as human primary culture cells to be used in the test.

Recently, it has been reported that commercially available drugs such as diabetes drugs or general anesthetics may cause cardiac arrhythmia, and interest in drug-induced cardiotoxicity is increasing. Accordingly, there is an urgent need to develop a cardiac cell model for drug development.

Under in vitro conditions, the embryonic stem cell-derived cardiomyocytes provided by the present invention are able to form cardiomyocyte bodies showing density and synchronized beating similar to the cardiac tissue, and thus they can be utilized for the development of a cardiac cell model for drug development.

Hereinafter, the present invention will be described in more detail with reference to Examples. However, these Examples are for illustrative purposes only, and the invention is not intended to be limited by these Examples.

Example 1: Production of Cardiomyocytes (CMs) from Human Embryonic Stem Cells (hESCs)

In vitro, three-dimensional differentiated aggregates, embryoid bodies (EBs) were formed from human embryonic stem cells (hESCs), and contracting cardiomyocytes (CMs) comprised therein were identified.

Example 1-1: hESC Culture and hEB Formation

Undifferentiated hESCs (CHA15-hESC and H9-hESC lines) were cultured on a mitotically inactive mouse embryonic fibroblast (MEF) feeder layer using DMEM/F12 (50: 50%; Gibco BRL, Gaithersburg, Md.) prepared by adding 20% (v/v) serum alternative (Gibco) to a basal hESC medium (1 mM L-glutamine, 1% non-essential amino acids, 100 mM beta-mercaptoethanol and 4 ng/mL bFGF). At this time, the DMEM/F12 medium was replaced every 24 hours, and the hESCs were transferred to the fresh mitotically inactive feeder layer using a cutting pipette every 5-7 days.

Subsequently, hESCs were isolated from the mitotically inactive feeder layer using dispase (Gibco), and transferred to an ultra-low attachment culture dish, and then a bFGF-free basal hESCs medium was added thereto, followed by suspension-culture for 2 days. Thereafter, the medium was replaced with DMEM supplemented with 20% FBS, and the cells were cultured for 15 to 20 days, and contracting three-dimensional differentiated aggregates, human embryoid bodies (hEBs) were formed from hESCs (FIG. 1, left panel). As shown in the left panel of FIG. 1, 10-15% of the formed EBs were contracted.

Example 1-2: Immunocytochemical Analysis of hEBs

In order to confirm whether the EBs contain contracting CMs, immunocytochemical analysis was performed using CM-specific markers.

In detail, the EBs were fixed in 4% paraformaldehyde on a slide glass for 20 minutes, and treated with PBS containing 0.1% Triton X-100 for 5 minutes. Subsequently, the cells were treated with 5% normal goat serum for 30 minutes, and then treated with primary antibodies (Millipore, Billerica, Mass.) which are specific to a CM-specific marker cTnT, followed by incubation at 4° C. for 12 hours for primary reaction. After terminating the primary reaction, the cells were washed with PBS three times, and treated with Rhodamine- or FITC-labeled secondary antibodies (Molecular Probes Inc., Eugene, Oreg.), followed by incubation for 1 hour for secondary reaction. After terminating the secondary reaction, the cells were washed with PBS three times, and stained. The stained slide was fixed in a glyceryl-based fixing solution containing 2.5% polyvinyl alcohol and 1,4-diazabicyclo (2.2.2) octane and 4,6-diamino-2-phenylindole (DAPI)(Sigma). The fixed slide was photographed under a LSM 510 META confocal microscope (Carl Zeiss Inc., Oberkochen, Germany), and analyzed (middle and right panels of FIG. 1). As shown in the middle and right panels of FIG. 1, partial staining of EBs was observed, indicating that contracting CMs were contained.

Example 1-3: Characterization of hEBs

The EBs were fixed on a gelatin-coated plate to perform hEB characterization (FIG. 2). As shown in the left panel of FIG. 2, a part of EBs was contracted even though fixed on the gelatin-coated plate. Next, as shown in the middle and right panels of FIG. 2, the result of immunocytochemical analysis of hEBs using the CM-specific markers cTnT and sMHC showed that the contracting area of hEBs was stained, but the non-contracting area of hEBs was not stained.

These results suggest that the hEBs contained contracting CMs and non-contracting cells.

Example 1-4: Analysis of Gene Expression Level of hEBs

The contracting area and the non-contracting area of hEBs were isolated by micro-dissection, and the isolated areas were treated with 0.25% trypsin-EDTA to isolate them at a cellular level. Each of the isolated cells was transferred to a gelatin-coated plate. qRT-PCR was carried out using the isolated cells to determine gene expression levels of the cardiac-related transcription factors (NKX2.5 and MEF-2c) and the cardiac-specific, sarcomeric protein-encoding genes (MLC-2v, MYH6, MYH7, and TnT).

In detail, total RNAs were obtained from each of the isolated cells using a TRIzol reagent (Molecular Research Center, Ohio), and RT-PCR was performed using 2 μg of the total RNAs and reverse transcriptase (SuperScript II reverse transcriptase) to synthesize cDNAs. qRT-PCR was performed by applying the synthesized cDNAs and each primer of the following Table 1 capable of amplifying the cardiac-related transcription factors (NKX2.5 and MEF-2c) and the cardiac-specific, sarcomeric protein-encoding genes (MLC-2v, MYH6, MYH7, and TnT) to an ABI 7300 qRT-PCR system (Applied Biosystems). At this time, GAPDH was used as a PCR internal control group, and gene expression levels were calculated by comparative ΔΔCt method (FIG. 3).

TABLE 1

| Gene | Name | Primer (5'-3') (SEQ ID No.) |
|---|---|---|
| GAPDH | NM002046.3 F | CATGTTCGTCATGGGTGTGAACCA (1) |
|  | NM002046.3 R | ATGGCATGGACTGTGGTCATGAGT (2) |
| NKx2.5 | NM001166175.1 F | CATCCTAAACCTGGAACAGCAGCA (3) |
|  | NM001166175.1 R | AGCGTAGGCCTCTGGCTTGAA (4) |
| MEF-2c | NM001131005.2 F | TCAACAGCACCAACAAGCTGTTCC (5) |
|  | NM001131005.2 R | TCAATGCCTCCACGATGTCTGAGT (6) |
| Myh6 | NM002471.3 F | ACCAAGTATGAGACGGACGCCATT (7) |
|  | NM002471.3 R | TCCAGTGAGGAGCACTTGGCATTA (8) |
| Myh7 | NM000257.2 F | CTGTTTGACAACCACCTGGGCAAA (9) |
|  | NM000257.2 R | TTGTTCTTCTGCAGCCAGCCAATG (10) |
| MLC-2v | NM182493.2 F | CAAGGACTTTGTTTCCCGGTTGCT (11) |
|  | NM182493.2 R | TTGGATCTTGAAGCTTTGGCAGGC (12) |
| cTnT | NM001001430.1 F | AGTTCGACCTGCAGGAGAAGTTCA (13) |
|  | NM001001430.1 R | TATTTCCAGCGCCCGGTGACTTTA (14) |

TABLE 1 -continued

| Gene | Name | Primer (5'-3') (SEQ ID No.) |
|---|---|---|
| FOXA2 | NM021784.4 F | ACTCGCTCTCCTTCAACGACTGTT (15) |
|  | NM021784.4 R | TTCTCGAACATGTTGCCCGAGTCA (16) |
| AFP | NM001134.1 F | TCTTCATATGCCAACAGGAGGCCA (17) |
|  | NM001134.1 R | ACTCTTGCTTCATCGTTTGCAGCG (18) |

As shown in FIG. 3, high expression levels of cardiac-related transcription factors and the cardiac-specific genes were observed in the contracting CMs.

Example 1-5: Immunocytochemical Analysis of Isolated hEBs

Immunocytochemical analysis of each cell of the hEBs isolated in Example 1-4 was performed using CM-specific markers cTnT and sMHC or endodermal cell markers FOXA2 and AFP. At this time, immunocytochemical analysis was performed in the same manner as in Example 1-2, except using cTnT or sMHC-specific primary antibodies (Millipore, Billerica, Mass.) and the endodermal cell marker, FoxA2- (Abcam Inc., Cambridge, Mass.) or AFP-specific primary antibodies (Abcam) (FIG. 4). As shown in FIG. 4, contracting cells were stained with the CM-specific markers, whereas non-contracting cells were stained with endodermal cell markers.

In addition, the result of immunocytochemical analysis using a mesodermal marker (Brachyury) and a nerve cell marker (TuJ1) showed that the cells isolated from hEBs were not stained, suggesting that hEBs contained contracting CMs and endodermal lineage-specific cells.

Taken together, the results of Examples 1-1 to 1-5 suggest that hEBs can be formed from hESCs in vitro, but they contain endodermal lineage-specific cells as well as CMs, and therefore, a step of purifying cardiomyoblasts from hEBs is required to produce CMs from hESCs.

Example 2: Purification of hESC-Derived CMs Using Serum-Free Medium

All of the cells isolated from hEBs in Example 1-4 were inoculated in a serum-free DMEM medium containing N2 supplement (N2 supplement, Gibco: 500 µg/ml insulin; 10,000 µg/ml human transferrin; 0.63 µg/ml progesterone; 1,611 µg/ml Putrascine; and 0.52 µg/ml Selenite) and in a DMEM medium containing 10% FBS and N2 supplement as a control, and then cultured for 2 weeks. Thereafter, each of the cultured cells was examined under a microscope to count the number of cells (left panels of FIGS. 5 and 6).

As shown in the left panels of FIGS. 5 and 6, there was no particular difference in the number of cells between the serum-free medium and the serum-containing medium, and contracting cells were also observed both in the serum-free medium and in the serum-containing medium, but non-contracting cells were observed only in the serum-containing medium, and not in the serum-free medium.

Meanwhile, immunostaining of the cultured cells was performed using DAPI (DAPI-expressing nuclei), and immunocytochemical analysis was performed using the CM-specific markers cTnT and sMHC at the same time (middle and right panels of FIGS. 5 and 6). As shown in the middle and right panels of FIGS. 5 and 6, the cells having DAPI-stained nuclei were mostly consistent with the cTnT and sMHC-positive cells when cultured in the serum-free medium (middle and right panels of FIG. 5), and a majority of the cells having DAPI-stained nuclei were not consistent with the cTnT and sMHC-positive cells when cultured in the serum-containing medium.

With respect to the DAPI positive cells, the numbers of cTnT and sMHC-positive cells were compared between the serum-free medium and the serum-containing medium (FIG. 7). As shown in FIG. 7, the numbers of cTnT and sMHC-positive cells were less than 50% in the serum-containing medium, but more than 80% in the serum-free medium.

Furthermore, gene expression levels of the cardiac-specific markers cTnT, Myh6, Myh7 and MLC-2v and endodermal lineage cell markers FOXA2 and AFP were compared between the cells cultured in the serum-free medium and in the serum-containing medium by qRT-PCR (FIG. 8). As shown in FIG. 8, the gene expression levels of the cardiac-specific markers were increased whereas the gene expression levels of endodermal lineage cell markers were decreased in the cells cultured in the serum-free medium.

Finally, to provide initial functional evaluation of hESC-derived CMs, whole-cell patch clamp recording of the contracting cells was performed. In detail, patch clamp recording of spontaneous action potential (AP) was carried out using an Axopatch 200B amplifier (Molecular Devices Corporation, Sunnyvale, Calif., USA) at a physiological temperature (37±1° C.). Cell-attached coverslips were placed in a recording chamber and perfused by an extracellular solution (137 mM NaCl, 5.4 mM KCl, 1.8 mM $CaCl_2$, 0.5 mM $MgCl_2$, 10 mM HEPES, 10 mM glucose, pH 7.4). The cells were examined under a microscope, and then selected for recording. Micropipettes had a tip resistance of 3-4 MΩ when filled with the intracellular solution (110 mM K-Asp, 10 mM KCl, 5 mM $MgCl_2$, 5 mM $Na_2ATP$, 10 mM EGTA and 1 mM $CaCl_2$, pH 7.2). After gigaohm seal formation, the membrane patch under the micropipette was disrupted by suction to establish whole cell patch-recording configuration. The series resistance was less than 5 MΩ. Data were sampled at 1 kHz, and recorded for approximately 5 to 10 minutes to assure AP stability. 5 recorded APs of the data were given as a mean value, and used for data analysis. Data acquisition and analysis were performed using pCLAMP 10.2 software (Molecular Devices Corporation). All compounds used in the preparation of the solutions were purchased from Sigma-Aldrich (Sigma).

As a result, 40 stable whole recordings of the purified and non-purified CMs from EBs were obtained under zero-current clamp conditions. In the records, three main classes of action potentials (nodal-type, atrial-type, and ventricular-type) were observed (FIG. 9). Cells having a ventricular-type action potential were most frequently observed under the serum-containing and serum-free culture conditions (Table 2).

TABLE 2

| | Total (N) | Nodal-type | | Atrial-type | | Ventricular-type | |
|---|---|---|---|---|---|---|---|
| | | Cluster (N) | Percentage (%) | Cluster (N) | Percentage (%) | Cluster (N) | Percentage (%) |
| H9 Serum-contained | 20 | 3 | 15 | 6 | 30 | 11 | 55 |
| H9 Serum-free | 20 | 1 | 5 | 2 | 10 | 17 | 85 |
| CHA15 Serum-contained | 20 | 4 | 20 | 7 | 35 | 9 | 45 |
| CHA15 Serum-free | 20 | 2 | 10 | 3 | 15 | 15 | 75 |

Interestingly, the ventricular-type action potentials were remarkably increased under the serum-free culture conditions, compared to the serum-containing culture conditions (FIG. 10). The similar result was also observed in CHA 15-human embryonic stem cell-derived CMs (FIG. 11).

Taken together, CMs can be more easily purified from embryoid bodies under the serum-free culture conditions.

Example 3: Proliferation Activity of hESC-Derived CMs

Contractility of the purified CMs was determined by a ratio of contracting cells present at a predetermined time to the number of the whole cells cultured in the serum-free medium. Because cell density is an important factor for maintaining cell functions and proliferation activity, Contractility and proliferation activity were compared between CMs purified at two different cell densities (low density of $1 \times 10^4$ cells/cm$^2$ and high density of $5 \times 10^4$ cells/cm$^2$). CMs at the low cell density bind in the form of single cells (left panel of FIG. 12), but most CMs at the high cell density bind in the form of colonies (right panel of FIG. 12, ▲). Overall, contractility of the purified CMs decreased over time. At the low cell density, only 38% of single CMs contracted after 2 weeks. However, at the high cell density, 90% of colonized CMs continuously contracted after 2 weeks. At the low cell density, contractility of single CMs was abruptly decreased at 2 weeks, and a few contracting cells (3%) were only observed at 6 weeks. In contrast, at the high density, 33% of the colonized CMs continuously contracted for additional 6 weeks (FIG. 13).

To evaluate proliferation activity of the cells, Ki-67 expression was analyzed. Ki-67 is present during all active phases of the cell cycle (G1, S, G2, and mitosis), but is absent from resting cells (G0). Single CMs without cell to cell contact showed no Ki-67 expression (left panel of FIG. 14). In the colonized CMs, the majority of Ki-67-expressing cells showed co-expression of sMHC (right panel of FIG. 14). Quantitative analysis showed that 3.4% of single cardiomyoblasts cultured at the low density and 48% of the colonized CMs cultured at the high density were Ki-67 positive (FIG. 15). Moreover, the number of CMs cultured at the high density increased over the culture period. 6 weeks after culture, the number of inoculated CMs was increased to approximately 75% at the high density, but less than 10% at the low density (FIG. 16).

These results suggest that human embryonic stem cell-derived CMs cultured at the high density can have improved proliferation ability.

Example 4: Production and Transplantation of CM Bodies (CBs)

Cardiomyocyte bodies (CBs) were produced and transplanted into the myocardial infarction-induced heart to examine their effects.

Example 4-1: Production of CBs

To improve the treatment success rate of hESC-derived CMs in cardiac diseases, hESC-derived CM bodies (CBs) were produced. In detail, purified hESC-derived CMs were suspension-cultured by a hanging drop method for 7 days to produce CBs having a diameter of 200 to 500 μm (FIG. 17). In particular, the produced CBs maintained synchronized beating (FIG. 18).

For characterization of the produced CBs, the CBs were transferred onto a gelatin-coated plate, and then immunocytochemical analysis was carried out using the cardiac-specific markers cTnT, Nkx2.5, Con43, and sMHC (FIGS. 19 to 21). The result showed that the cardiac-specific markers cTnT, Nkx2.5, Con43, and sMHC were expressed in the CBs.

Example 4-2: Induction of Myocardial Infarction and Transplantation of CBs

In accordance with the known method, myocardial infarction was induced in the thymus-free male Sprague Dawley rats (Rh-rnu/rnu, 200-250 g, Harlan, Seoul, Korea) by left coronary artery ligation (K. Suzuki, et al., Circulation, 104(12 Suppl 1):1207, 2001; L. E. Wold, et al., Methods Mol. Med., 139:355, 2007). In detail, the rats were anesthetized with 3% Isoflurane (Choongwae Pharma Corp., Seoul, Korea, http://www.jw-pharma.co.kr), and then anesthesia was maintained with 2% Isoflurane. After endrotracheal intubation of the anesthetized rats, mechanical ventilation was commenced with 0.2 ml of the average inhaled volume at a rate of 70 beats/min. The heart was exposed through a left thoracotomy, and the left coronary artery was permanently sutured with 7-0 silk by coursing between the pulmonary artery and the left atrial appendage. After coronary artery occlusion in rats, the anterior left ventricle wall infarction was confirmed by the presence of pale color of the anterior wall and reduced myocardial motion.

Subsequently, 100 μl of a solution containing the purified CMs or CBs ($5 \times 10^6$ cells) was injected into the boundary zone surrounding the infarct area immediately after left coronary artery occlusion using a syringe with a 29 G needle (FIG. 22). After recovery from the surgery, the rats were transferred to cages. The echocardiographic inclusion criterion was fractional shortening less than 30% (FIG. 23).

At 7 weeks after CB transplantation, the rats were sacrificed, and the control group transplanted with purified CM was compared with the experimental group transplanted with CBs.

First, no teratoma formation was detected in the control group and the experimental group, indicating that the transplanted CMs and CBs have no stem cell differentiation capability, because the teratomas are formed upon transplantation of stem cells having differentiation capability.

Next, the cardiac tissue of each rat was stained with hematoxylin-eosin (FIG. 24). As shown in FIG. 24, more extensive tissue regeneration was observed in the CB-transplanted experimental group (right) than the CM-transplanted control group (left).

Further, the cardiac tissue of each rat was stained with Masson's trichrome (FIG. 25). As shown in FIG. 25, less fibrous tissue was observed in the CB-transplanted experimental group (right) than the CM-transplanted control group (left).

Further, bulky cardiac muscle tissue was detected in the CB-transplanted experimental group (right) than the CM-transplanted control group (left) (FIG. 26).

Furthermore, before transplantation of the cardiac tissue, the cardiac tissue was treated with a fluorescent DiI, and immunocytochemical analysis of the DiI-treated cardiac tissue was performed using a nuclear marker DAPI and various cardiac-specific markers cTnT, Merge or Con43. As a result, cardiac muscle regeneration by transplantation of CBs was observed in the infarction-induced area (FIGS. 27 to 34). In particular, more extensive presence of DiI-positive cells were observed in transplantation of CBs than in transplantation of CMs (FIGS. 28 and 29), and the Con43-positive cells localized in the DiI-positive cell-detected area (FIG. 30). A few sporadic transplants were observed between transplanted CBs and CMs in the boundary zone (FIGS. 31 to 34). However, engraftment of DiI-positive cells or Con43 was not observed in the CM-transplanted control group (FIG. 35).

Example 4-3: Effect of Transplanted CBs on Left-Ventricular (LV) Function

Echocardiography was performed to evaluate and compare functional properties of the infarcted heart. Non-infarcted rats were used to generate the default value (FIG. 36), and infarcted rats having echocardiographic fractional shortening (FS) of less than 30% were selected from each group on day 2 after transplantation (FIGS. 37 to 39, left panel). In addition, the hearts of the rats were re-evaluated by echocardiography on day 51 after transplantation (37 to 39, right panel).

At this time, echocardiographic studies were performed using a VIVID 7 dimension system (General Electric-Vingmed Ultrasound, Horton Norway) at MI surgery, before cell transplantation and after 4 weeks. Images were obtained by using an i13L transducer (5.3-14.0 MHz) mounted in the chest wall with high temporal and spatial resolution. The complete two-dimensional and M-mode echocardiography was performed under anesthesia. Peak systolic strain values were measured in each of 5 cardiac cycles using a zoomed image window. The maximum and minimum values were discarded, and the mean value was calculated from the rest 3 values. The images and 2D deformed images reconstructed offline were compared in each rat, and were interpreted by two investigators without prior information. 2D deformation and deformation rate were calculated by the known method (J. Hartmann, et al., Cardiovasc Ultrasound, 5:23, 2007).

First, echocardiography of the non-myocardial infarcted rats was carried out on day 2 after transplantation, and the result showed that left-ventricular internal diastolic dimension (LVIDd) was 0.66±0.1 cm, left-ventricular internal dimension in systole (LVIDs) was 0.36±0.07 cm and fractional shortening (FS) was 45.95±5.03% (Table 3).

TABLE 3

| | Group | Day 2 | Day 51 |
|---|---|---|---|
| LVIDs (cm) | Control | 0.596 ± 0.114586 | 0.700 ± 0.090000 |
| | Single | 0.588 ± 0.085849 | 0.666 ± 0.080808 |
| | CBs | 0.630 ± 0.093005 | 0.536 ± 0.068044 |
| | Non-infarcted | 0.364 ± 0.079875 | — |
| LVIDd (cm) | Control | 0.756 ± 0.132401 | 0.812 ± 0.080436 |
| | Single | 0.746 ± 0.085615 | 0.868 ± 0.070143 |
| | CBs | 0.760 ± 0.105594 | 0.794 ± 0.096333 |
| | Non-infarcted | 0.666 ± 0.109225 | — |
| FS (%) | Control | 21.536 ± 2.830765 | 13.728 ± 4.824243 |
| | Single | 21.340 ± 5.202009 | 23.158 ± 5.907044 |
| | CBs | 17.450 ± 4.435076 | 32.204 ± 4.210888 |
| | Non-infarcted | 45.952 ± 5.031329 | — |

On the same day, the infarcted rats showed similar ventricular expansion and reduced fractional shortening, irrespective of being transplanted with nothing, transplanted with CMs or transplanted with CBs. Overall, the rats showed 15% increase in LVIDd, 75% increase in LVIDs and 62% decrease in fractional shortening, compared to the non-infarcted rats.

On day 51 after transplantation, the infarcted ischemic heart transplanted with CMs or CBs showed increased ventricular expansion, compared to those on day 2 (FIGS. 38 and 39). In this regard, non-transplanted rats showed LVIDs of 0.7±0.09 cm, CM-transplanted rats showed LVIDs of 0.66±0.08 cm, whereas CB-transplanted rats showed LVIDs of 0.53±0.06 cm. Non-transplanted or CM-transplanted rats showed remarkably increased LVIDs, compared to those measured on day 2, whereas CB-transplanted rats showed reduced LVIDs, compared to those measured on day 2 (FIG. 40).

Further, LVIDd values measured on day 51 were mostly higher than those measured on day 2, but CB-transplanted rats showed the lowest increase level of LVIDd, compared to non-transplanted or CM-transplanted rats (FIG. 41).

Furthermore, left ventricular contraction measured by fractional shortening (FS) was remarkably decreased in the control heart over the 7-week test period, and decreased to the level of 13.72±4.82% in non-transplanted rats. CM-transplanted rats showed slightly increased fractional shortening values (23.15±5.90%) on day 51, compared to the values (21.34±5.20%) measured on day 2. CB-transplanted rats showed remarkably increased fractional shortening values, compared to non-transplanted or CM-transplanted rats (FIG. 42).

Taken together, when CBs are transplanted into the ischemic heart of the myocardial infarcted rat, ventricular expansion (LVIDs, LVIDd) was decreased, compared to non-transplanted or CM-transplanted rats, which slows the progression of heart failure and also improves fractional shortening, thereby improving the function of the left cardiac ventricle.

EFFECT OF THE INVENTION

The method for producing cardiomyocytes of the present invention can used to easily purify embryonic stem cell-differentiated cardiomyocytes without additional equipment. Further, the purified cardiomyocytes can be used to produce cardiomyocyte bodies, which can be used as a cellular therapeutic agent for treating cardiac diseases. Therefore, the cardiomyocyte bodies can be widely applied to the development of prophylactic or therapeutic agents for cardiac diseases.

What is claimed is:

1. A method for producing cardiomyocytes from human or mouse embryonic stem cells, comprising: (a) culturing said embryonic stem cells in a suspension culture to obtain embryoid bodies; (b) isolating cells from the embryoid bodies to produce a cell population; and (c) culturing the population of cells isolated from the embryoid bodies in a medium consisting of a serum-free medium and N2 supplement for at least two weeks to kill cells other than cardiomyocytes, thereby producing a cell population comprising more than 80% of cardiomyocytes that express cTnT and sMHC.

2. The method according to claim 1, wherein the medium consisting of a serum-free medium and N2 supplement is a medium consisting of a DMEM medium and N2 supplement.

3. The method according to claim 1, further comprising disassociating obtained embryoid bodies into single cells.

4. The method according to claim 1, wherein the cardiomyocytes: (i) express at least one marker selected from the group consisting of a-actinin, troponin I (cTnI), AN P, GATA4, Nkx2.5, MEF-2c, MYH6, MYH7, Con43, myosin heavy chain (a-MHC or sMHC), myosin light chain (MLC-2a or MLC-2v) and cardiac actin; (ii) have a cyst-like shape, a mixed shape, a floating or muscle-like shape; and (iii) exhibit pulsatile beating.

5. A method for producing cardiomyocyte bodies from human or mouse embryonic stem cells, comprising: (a) culturing said embryonic stem cells in a suspension culture to obtain embryoid bodies; (b) isolating cells from the embryoid bodies to produce a cell population; (c) culturing the population of cells isolated from the embryoid bodies in a medium consisting of a serum-free medium and N2 supplement for at least two weeks to kill cells other than cardiomyocytes, thereby producing a cell population comprising more than 80% of cardiomyocytes that express cTnT and sMHC; (d) isolating cardiomyocytes from the cells of step (c); and (e) suspension culturing the cardiomyocytes of step (d) for at least 7 days to produce cardiomyocyte bodies.

6. The method according to claim 5, wherein the serum-free medium consisting of a serum-free medium and N2 supplement is a medium consisting of a DMEM medium and N2 supplement.

7. The method according to claim 5, wherein the cardiomyocyte bodies exhibit synchronized beating.

8. The method according to claim 5, wherein the cardiomyocyte bodies have a diameter of 200 to 500 um.

* * * * *

SEQUENCE LISTING

```
<160> NUMBER OF SEQ ID NOS: 18

<210> SEQ ID NO 1
<211> LENGTH: 24
<212> TYPE: DNA
<213> ORGANISM: Artificial Sequence
<220> FEATURE:
<223> OTHER INFORMATION: NM002046.3 primer F

<400> SEQUENCE: 1
catgttcgtc atgggtgtga acca                                             24

<210> SEQ ID NO 2
<211> LENGTH: 24
<212> TYPE: DNA
<213> ORGANISM: Artificial Sequence
<220> FEATURE:
<223> OTHER INFORMATION: NM002046.3 primer R

<400> SEQUENCE: 2
atggcatgga ctgtggtcat gagt                                             24

<210> SEQ ID NO 3
<211> LENGTH: 24
<212> TYPE: DNA
<213> ORGANISM: Artificial Sequence
<220> FEATURE:
<223> OTHER INFORMATION: NM001166175.1 primer F

<400> SEQUENCE: 3
catcctaaac ctggaacagc agca                                             24

<210> SEQ ID NO 4
<211> LENGTH: 21
<212> TYPE: DNA
<213> ORGANISM: Artificial Sequence
<220> FEATURE:
<223> OTHER INFORMATION: NM001166175.1 primer R

<400> SEQUENCE: 4
agcgtaggcc tctggcttga a                                                21

<210> SEQ ID NO 5
<211> LENGTH: 24
<212> TYPE: DNA
<213> ORGANISM: Artificial Sequence
<220> FEATURE:
<223> OTHER INFORMATION: NM001131005.2 primer F

<400> SEQUENCE: 5
tcaacagcac caacaagctg ttcc                                             24

<210> SEQ ID NO 6
<211> LENGTH: 24
<212> TYPE: DNA
<213> ORGANISM: Artificial Sequence
<220> FEATURE:
<223> OTHER INFORMATION: NM001131005.2 primer R

<400> SEQUENCE: 6
tcaatgcctc cacgatgtct gagt                                             24

<210> SEQ ID NO 7
<211> LENGTH: 24
<212> TYPE: DNA
<213> ORGANISM: Artificial Sequence
```

```
<220> FEATURE:
<223> OTHER INFORMATION: NM002471.3 primer F

<400> SEQUENCE: 7
accaagtatg agacggacgc catt                                              24

<210> SEQ ID NO 8
<211> LENGTH: 24
<212> TYPE: DNA
<213> ORGANISM: Artificial Sequence
<220> FEATURE:
<223> OTHER INFORMATION: NM002471.3 primer R

<400> SEQUENCE: 8
tccagtgagg agcacttggc atta                                              24

<210> SEQ ID NO 9
<211> LENGTH: 24
<212> TYPE: DNA
<213> ORGANISM: Artificial Sequence
<220> FEATURE:
<223> OTHER INFORMATION: NM000257.2 primer F

<400> SEQUENCE: 9
ctgtttgaca accacctggg caaa                                              24

<210> SEQ ID NO 10
<211> LENGTH: 24
<212> TYPE: DNA
<213> ORGANISM: Artificial Sequence
<220> FEATURE:
<223> OTHER INFORMATION: NM000257.2 primer R

<400> SEQUENCE: 10
ttgttcttct gcagccagcc aatg                                              24

<210> SEQ ID NO 11
<211> LENGTH: 24
<212> TYPE: DNA
<213> ORGANISM: Artificial Sequence
<220> FEATURE:
<223> OTHER INFORMATION: NM182493.2 primer F

<400> SEQUENCE: 11
caaggacttt gtttcccggt tgct                                              24

<210> SEQ ID NO 12
<211> LENGTH: 24
<212> TYPE: DNA
<213> ORGANISM: Artificial Sequence
<220> FEATURE:
<223> OTHER INFORMATION: NM182493.2 primer R

<400> SEQUENCE: 12
ttggatcttg aagctttggc aggc                                              24

<210> SEQ ID NO 13
<211> LENGTH: 24
<212> TYPE: DNA
<213> ORGANISM: Artificial Sequence
<220> FEATURE:
<223> OTHER INFORMATION: NM001001430.1 primer F

<400> SEQUENCE: 13
agttcgacct gcaggagaag ttca                                              24
```

```
<210> SEQ ID NO 14
<211> LENGTH: 24
<212> TYPE: DNA
<213> ORGANISM: Artificial Sequence
<220> FEATURE:
<223> OTHER INFORMATION: NM001001430.1 primer R

<400> SEQUENCE: 14
tatttccagc gcccggtgac ttta                                              24

<210> SEQ ID NO 15
<211> LENGTH: 24
<212> TYPE: DNA
<213> ORGANISM: Artificial Sequence
<220> FEATURE:
<223> OTHER INFORMATION: NM021784.4 primer F

<400> SEQUENCE: 15
actcgctctc cttcaacgac tgtt                                              24

<210> SEQ ID NO 16
<211> LENGTH: 24
<212> TYPE: DNA
<213> ORGANISM: Artificial Sequence
<220> FEATURE:
<223> OTHER INFORMATION: NM021784.4 primer R

<400> SEQUENCE: 16
ttctcgaaca tgttgcccga gtca                                              24

<210> SEQ ID NO 17
<211> LENGTH: 24
<212> TYPE: DNA
<213> ORGANISM: Artificial Sequence
<220> FEATURE:
<223> OTHER INFORMATION: NM001134.1 primer F

<400> SEQUENCE: 17
tcttcatatg ccaacaggag gcca                                              24

<210> SEQ ID NO 18
<211> LENGTH: 24
<212> TYPE: DNA
<213> ORGANISM: Artificial Sequence
<220> FEATURE:
<223> OTHER INFORMATION: NM001134.1 primer R

<400> SEQUENCE: 18
actcttgctt catcgtttgc agcg                                              24
```